(12) United States Patent
Kudo et al.

(10) Patent No.: US 6,407,284 B1
(45) Date of Patent: Jun. 18, 2002

(54) METHOD OF RESOLVING 2-OXOBICYCLO [3.1.0] HEXANE-6-CARBOXYLIC ACID DERIVATIVES

(75) Inventors: Junko Kudo, Ibaraki; Yoshiki Takashima, Nishinomiya; Sanae Mine, Ibaraki, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/549,564

(22) Filed: Apr. 14, 2000

(30) Foreign Application Priority Data

Apr. 16, 1999 (JP) .............................. 11-109645

(51) Int. Cl.⁷ .............................................. C07B 55/00
(52) U.S. Cl. ........................................ 562/401; 435/136
(58) Field of Search ........................... 435/136; 562/401

(56) References Cited

U.S. PATENT DOCUMENTS 5,405,763 A * 4/1995 Nishizawa et al.
5,476,965 A * 12/1995 Chase et al.
5,661,184 A * 8/1997 Helton et al.

FOREIGN PATENT DOCUMENTS

| EP | 846769 A2 | * | 10/1998 |
| EP | 846769 A2 | * | 10/1998 |
| JP | 407213280 A | * | 8/1995 |
| JP | 407213280 A | * | 8/1995 |
| JP | 8188561 | | 7/1996 |
| WO | WO9604900 | | 2/1996 |
| WO | WO9701526 | | 1/1997 |

* cited by examiner

Primary Examiner—Louise N. Leary
Assistant Examiner—Hector M Reyes
(74) Attorney, Agent, or Firm—Birch, Stewart, Kolasch & Birch, LLP

(57) ABSTRACT

There is disclosed a method of resolving 2-oxobicyclo [3.1.0]hexane-6-carboxylates having the following relative configuration of formula (1):

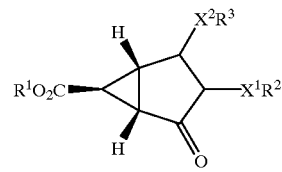

wherein $X^1$, $X^2$, $R^1$, $R^2$ and $R^3$ have the same meanings as defined below, into one enantiomer ester thereof and the other enantiomer acid,
which is characterized by
contacting an enzyme having an ability to preferentially hydrolyze one enantiomer ester contained in 2-oxobicyclo[3.1.0]hexane-6-carboxylate of formula (1) as defined above, with 2-oxobicyclo[3.1.0] hexane-6-carboxylates of formula (1) as defined above to obtain one enantiomer as an acid and the other enantiomer as an ester.

13 Claims, 3 Drawing Sheets

METHOD OF RESOLVING 2-OXOBICYCLO [3.1.0] HEXANE-6-CARBOXYLIC ACID DERIVATIVES

BACKGROUND OF THE INVENTION

1. Field of the Invention

The present invention relates to a method of resolving 2-oxobicyclo [3.1.0]hexane-6-carboxylic ester into an optically active acid or ester derivative thereof.

2. Description of Related Art

Optically 2-oxobicyclo[3.1.0]hexane-6-carboxylic acids and ester compounds thereof are useful intermediate compounds for pharmaceutical preparations etc.

As the method of preparing said optically active 2-oxobicyclo[3.1.0]hexane-6-carboxylic acids, a method of optical resolution and a method of derivatizing them from optically active substances have been known in the art.

As the method of optical resolution, for example a method of optical resolution of racemic (1SR,5RS,6SR)-2-oxobicyclo[3.1.0]hexane-6-carboxylic acids by using an optically active amine such as optically active phenethylamine as an optically resolving agent has been known (JP-A 08-188561, WO 96/04900).

As the method of derivatizing them from optically active substances, a method of derivatizing optically active 2-oxobicyclo[3.1.0]hexane-6-carboxylic acids from optically active dicyclopentane dienone as the starting material has been known (JP-A 08-188561).

However, they have problems in that in industrial production, the method of optical resolution requires a recycling step of recovering the optically resolving agent, thus increasing the number of steps, while the method of derivatizing them from optically active substances makes use of the optically active compound as the starting material, thus raising the cost of the starting material.

SUMMARY OF THE INVENTION

An object of the invention is to provide a method of resolving 2-oxobicyclo[3.1.0]hexane-6-carboxylate into acid and ester derivatives thereof, without using any optically resolving agent, by selectively hydrolyzing an optional optical isomer of 2-oxobicyclo[3.1.0]hexane-6-carboxylates, thereby efficiently producing the desired compound with an enzyme.

The present invention provides:

1. a method of resolving 2-oxobicyclo[3.1.0]hexane-6-carboxylates having the following relative configuration of formula (1):

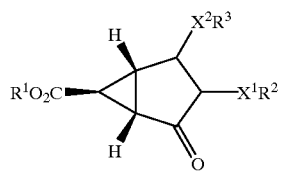

wherein $X^1$, $X^2$, $R^1$, $R^2$ and $R^3$ have the same meanings as defined below, into one enantiomer ester thereof and the other enantiomer acid, which comprises:

contacting an enzyme having an ability to preferentially hydrolyze one enantiomer ester contained in 2-oxobicyclo[3.1.0]hexane-6-carboxylate of formula (1) as defined above, with 2-oxobicyclo[3.1.0]hexane-6-carboxylate of formula (1) as defined above to obtain one enantiomer as an acid and the other enantiomer as an ester, wherein $R^1$ represents a $C_1$ to $C_{10}$ alkyl group which may be substituted with at least one group selected from a $C_1$ to $C_8$ alkoxy, halogen or nitro;

an allyl group;

an arylalkyl group which aryl may be substituted with at least one group selected from a $C_1$ to $C_8$ alkyl, $C_1$ to $C_8$ alkoxy, halogen or nitro group; or an aryl group which may be substituted with at least one group selected from a $C_1$ to $C_8$ alkyl, $C_1$ to $C_8$ alkoxy, halogen or nitro;

$X^1$ and $X^2$ independently represent a single bond, S, O, SO, $SO_2$ or $NR^4$ wherein $R^4$ represents a hydrogen or a group of formula: $(CO)nR^5$ wherein n is 0 or 1, and $R^5$ represents a hydrogen atom or a halogen atom;

a $C_1$ to $C_{10}$ allyl group which may be substituted with at least one group selected from a $C_1$ to $C_8$ alkoxy, hydroxy, halogen, amino, nitro, thiol or thioalkyl;

a $C_2$ to $C_{10}$ alkenyl group which may be substituted with at least one group selected from a $C_1$ to $C_8$ alkoxy, hydroxy, halogen, amino, nitro, thiol or thioalkyl;

a $C_2$ to $C_{10}$ alkynyl group which may be substituted with at least one group selected from a $C_1$ to $C_8$ alkoxy, hydroxy, halogen, amino, nitro,. thiol or thioalkyl;

an aryl group which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl;

an arylalkyl group wherein the aryl may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl;

an aromatic heterocyclic ring which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl; or a non-aromatic heterocyclic ring which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl;

$R^2$ and $R^3$ independently represent hydrogen, a halogen atom or a nitro group;

a $C_1$ to $C_{10}$ alkyl group which may be substituted with at least one group selected from a $C_1$ to $C_8$ alkoxy, hydroxy, halogen, amino, nitro, thiol or thioalkyl;

a $C_2$ to $C_{10}$ alkenyl group which may be substituted with at least one group selected from a $C_1$ to $C_8$ alkoxy, hydroxy, halogen, amino, nitro, thiol or thioalkyl;

a $C_2$ to $C_{10}$ alkynyl group which may be substituted with at least one group selected from a $C_1$ to $C_8$ alkoxy, hydroxy, halogen, amino, nitro, thiol or thioalkyl;

an aryl group which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl;

an arylalkyl group, which aryl may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl;

an aromatic heterocyclic ring which may be substituted with at least one group selected from a $C_1$ to $C_8$ allyl, $C_2$ to $C_8$ alkenyl, $C_2$ to $C_8$ alkynyl, $C_1$ to $C_8$ alkoxy, hydroxy, halogen, amino, nitro, thiol or thioalkyl;

a non-aromatic heterocyclic ring which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl;

a non-aromatic hydrocarbon ring which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl, said non-aromatic hydrocarbon ring being condensed with 1 or 2 aromatic hydrocarbon rings or aromatic heterocyclic rings; or a non-aromatic heterocyclic ring which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl, said non-aromatic heterocyclic ring being condensed with 1 or 2 aromatic hydrocarbon rings or aromatic heterocyclic rings.

Hereinafter, the above-described method is referred to as the present method.

DESCRIPTION OF THE PREFERRED EMBODIMENTS

Figure 1:
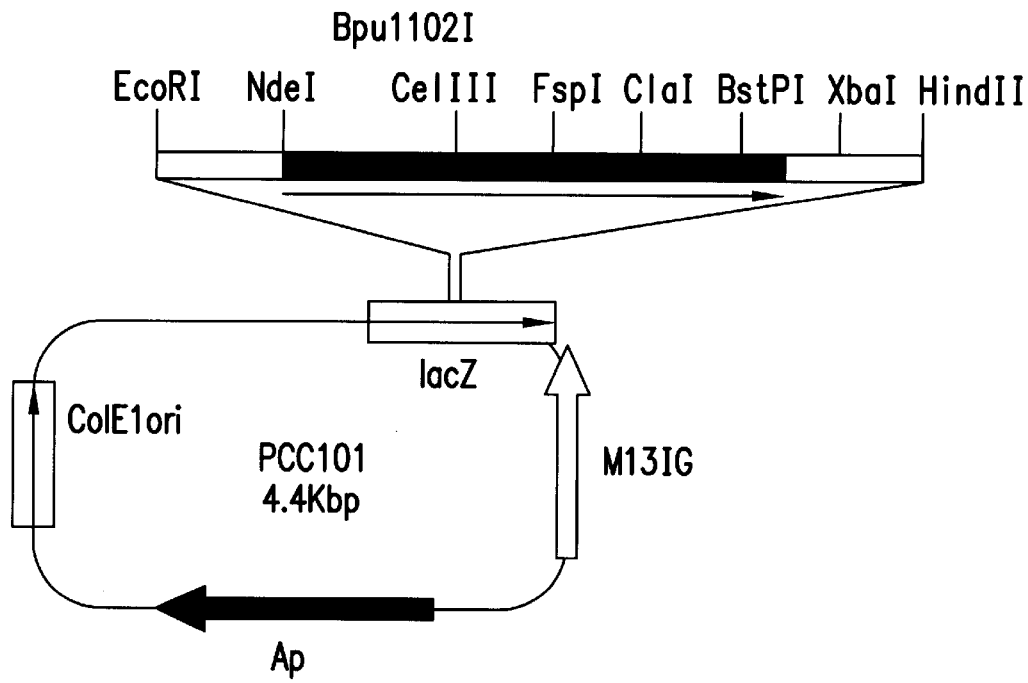
FIG. 1 shows a restriction enzyme map of expression plasmid pCC101. In this drawing, regions of blank square are DNA derived from Chromobacterium SC-YM-1 (FERM BP-6703 transferred from FERM P-14009), and a region of thick line is a coding region for the present enzyme (wild-type) derived from Chromobacterium SC-YM-1 (FERM BP-6703 transferred from FERM P-14009).

First a description will be made to a method of resolving 2-oxobicyclo[3.1.0]hexane-6-carboxylates having the relative configuration of formula (1) into one enantiomer ester thereof and the other enantiomer acid, which comprises:
contacting an enzyme having an ability to preferentially hydrolyze one enantiomer ester contained in 2-oxobicyclo[3.1.0]hexane-6-carboxylate of formula (1) as defined above, with 2-oxobicyclo[3.1.0] hexane-6-carboxylate of formula (1) as defined above to obtain one enantiomer as an acid and the other enantiomer as an ester The 2-oxobicyclo[13.1.0]hexane-6-carboxylate of formula (1), used as the starting material in the method of the present invention, are synthesized by various methods such as the method of James A. Monn et al. (Journal of Medicinal Chemistry, 1997, Vol. 40, No. 4, 528–537).

The 2-oxobicyclo[3.1.0]hexane-6-carboxylates having the relative configuration of formula (1) include two enantiomer esters (3a) and (3b) having the following absolute configurations with respect to the asymmetric carbon atoms at the 1-, 5- and 6-positions:

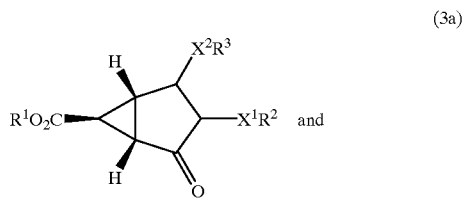

(3a)

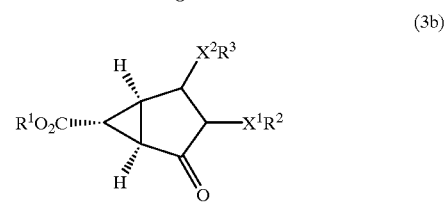

(3b)

wherein $X^1$, $X^2$, $R^1$, $R^2$ and $R^3$ have the same meanings as defined above.

In the present invention, one of the above-described enantiomers are selectively hydrolyzed to the corresponding enantiomer acid having an absolute configuration of formulae:

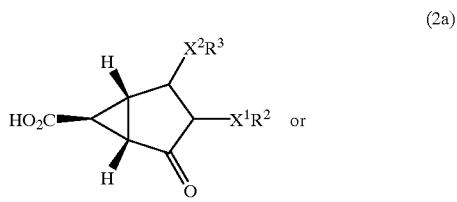

(2a)

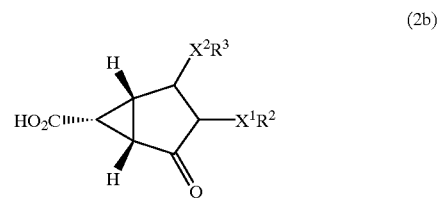

(2b)

wherein $X^1$, $X^2$, $R^2$ and $R^3$ have the same meanings as defined above, respectively, according to the enzyme employed.

In the present method, 2-oxobicyclo[3.1.0]hexane-6-carboxylate of formula (1'):

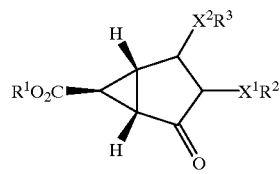

wherein $X^1$, $X^2$, $R^1$, $R^2$ and $R^3$ have the same meanings as defined above, which usually includes 4 optically active isomers based on the asymmetric carbon atoms at the 1-, 5- and 6-positions may be subjected to contacting with the present enzyme as described above for the compound of formula (1) above. Examples of the optical isomers include (3a), (3b), (4a) and (4b), the last two of which have the following formulae:

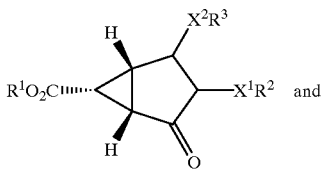
(4a)

and

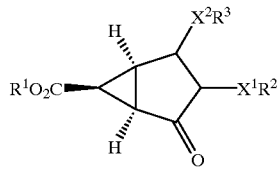
(4b)

wherein $X^1$, $X^2$, $R^1$, $R^2$ and $R^3$ have the same meanings as defined above.

Preferential hydrolysis with the present enzyme usually produces one acid of formula (2a) or (2b) and a diastereomeric mixture of esters of formulae (4a), (4b) and one selected from the compound of formula (3a) or (3b). One compound of formula (3a) or (3b) that was not hydrolyzed can be separated readily by column chromatography or the like from the resulting diastereomeric mixture.

The 2-oxobicyclo[3.1.0]hexane-6-carboxylates of formula (1) or (1'), which can be used in the method of the present invention, may be a mixture containing these optically active isomers in an equal amount respectively, or in a optional ratio. One of the optically active isomer may be contained in excess.

In the chemical formulae of the present invention, some of the substituent groups are defined as below.

The "$C_1$ to $C_{10}$ alkyl" refers to a straight-chain, branched or cyclic alkyl chain containing 1 to 10 carbon atoms. For example, specific examples of the straight-chain or branched $C_1$ to $C_{10}$ alkyl include methyl, ethyl, n-propyl, isopropyl, n-butyl, isobutyl, sec-butyl, t-butyl, n-pentyl, isopentyl, neopentyl, n-hexyl, 2-methylpentyl, 3-methylpentyl, 4-methylpentyl, 2,2-dimethylbutyl, 2,3-dimethylbutyl, 3,3-dimethylbutyl, heptyl, n-octyl, 2,2-dimethylhexyl, 2,5-dimethylhexyl, 2-methylheptyl, 4-methylheptyl, 2,2,4-trimethylpentyl, 2,3,4-trimethylpentyl, nonyl, 3,4,5-trimethylpentyl, decyl, and 3,7-dimethyloctyl.

The cyclic alkyl group includes e.g. monocyclic alkyl groups such as cyclopropyl, cyclobutyl, cyclopentyl, cyclohexyl, cycloheptyl, cyclooctyl, cyclononyl and cyclodecyl, or fused cyclic alkyl groups such as 1-adamantyl, 2-adamantyl, 1-decalyl, 2-decalyl, 4decalyl, bicyclo[3.3.0]oct-1-yl, -2-yl or -3-yl, bicyclo[4.3.0]non-1-yl, -2-yl, -3-yl or -7-yl, bicyclo[5.3.0]dec-1-yl, -2-yl, -3-yl, -4-yl, -8-yl, -9-yl, or bicyclo[3.3.1]non-1-yl, -2-yl, -3-yl or -9-yl.

The "$C_2$ to $C_{10}$ alkenyl group" refers to a straight-chain or branched unsaturated hydrocarbon chain containing 2 to 10 carbon atoms, having one or more carbon-carbon double bonds (diene, triene etc.). This group includes both E-isomer(s) and Z-isomer(s).

Typical examples thereof include vinyl, allyl, allenyl, 1-butenyl, 2-butenyl, 2-methyl-1-propenyl, butadienyl, 1-pentenyl, 2-pentenyl, 2-methyl-2-butenyl, 4-pentenyl, 3-methyl-2-butenyl, 3-methyl-1,2-butadienyl, 3-hexenyl, 2-hexenyl, 4-methyl-3-pentenyl, 4-hexenyl, 5-hexenyl, 3-methyl-1-pentene-3-yl, 6-methyl-5-heptene-2-yl, 7-octenyl, 1-octene-3-yl, 3-nonenyl, 2,4-dimethyl-2,6-heptadienyl, 3,7-dimethyl-6-octenyl, 5-decenyl, 9-decenyl and 2,6-dimethyl-7-octenyl.

Examples of the $C_1$ to $C_4$ alkoxy includes e.g. methoxy, ethoxy, n-propoxy, isopropyl, n-butoxy, sec-butoxy and t-butoxy.

The "halogen atom" means a fluorine, chlorine, bromine or iodine atom.

Examples of the aryl group include an ($C_6$–$C_{12}$) aromatic group such as a phenyl, naphthyl and biphenyl group. Typical examples thereof include 1-naphthyl, 2-naphthyl, phenyl, 2-biphenyl, 3-biphenyl, 4biphenyl.

The "arylalkyl" refers to a $C_1$ to $C_4$ alkyl group having one or more ($C_6$–$C_{12}$)aryl groups. Typical examples thereof include a benzyl, 1-phenylethyl, 2-phenylethyl, 3-phenylpropyl, 4-phenylbutyl, 2-methyl-2-phenylpropyl, triphenylmethyl, diphenylmethyl, and α-naphthyldiphenylmethyl.

Examples of the "aromatic heterocyclic ring" includes an aromatic 5- to 6-memberred ring containing 1 to 4 heteroatoms selected from oxygen, sulfur and nitrogen, and also a bicyclic ring composed of an aromatic 5- to 6-memberred ring containing 1 to 4 heteroatoms selected from oxygen, sulfur and nitrogen and either a benzene ring or an aromatic 5- to 6-memberred ring containing 1 to 4 heteroatoms selected from oxygen, sulfur and nitrogen.

Typical examples thereof include furyl, thiophenyl, oxazolyl, isoxazolyl, thiazolyl, isothiazolyl, imidazolyl, pyrimidyl, benzofuryl, benzothiophenyl, benzimidazolyl, benzoxazolyl, benzothiazolyl and indolyl groups.

The "non-aromatic heterocyclic ring" includes a 4- to 7-memberred ring containing 1 or 2 heteroatoms selected from oxygen, sulfur and nitrogen.

Typical examples thereof include an azetidine-1-yl or -2-yl group,
  a pyrrolidine-1-yl, -2-yl or -3-yl group,
  a piperidine-1-yl, -2-yl, -3-yl or -4-yl group,
  a hexahydroazepin-1-yl, -2-yl, -3-yl or -4-yl group,
  an oxetane-2-yl or -3-yl group,
  a tetrahydrofuran-2-yl or -3-yl group,
  a tetrahydropyran-2-yl, -3-yl or -4-yl group,
  a hexahydroxepin-2-yl, -3-yl or -4-yl group,
  a thiethane-2-yl or -3-yl group,
  a tetrahydrothiophiene-2-yl or -3-yl group,
  a tetrahlydrothiopyran-2-yl, -3-yl or -4-yl group,
  a hexahydrothiepin-2-yl,-3-yl or -4-yl group,
  a piperazine-1-yl or -2-yl group,
  a morpholine-1-yl, -2-yl or -3-yl group,
  a thiomorpholine-1-yl, -2-yl or -3-yl group,
  a tetrahydropyrimidine-1-yl, -2-yl, -4-yl or -5-yl group,
  an imidazoline-1-yl, -2-yl or -4-yl group,
  an imidazolidine-1-yl, -2-yl or -4-yl group,
  an oxazoline-2-yl, -3-yl, -4-yl or -5-yl group,
  an oxazolidine-2-yl, -3-yl, -4-yl or -5-yl group,
  a thiazoline-2-yl, -3-yl, -4-yl or -5-yl group, and
  a thiazolidine-2-yl, -3-yl, -4-yl or -5-yl group.

Examples of the non-aromatic hydrocarbon ring condensed with 1 or 2 aromatic hydrocarbon rings or aromatic heterocyclic rings" includes a group wherein a $C_8$ to $C_{10}$ cyclic alkyl group has been condensed with a benzene ring or with an aromatic 5- to 6-memberred aromatic ring containing 1 to 4 heteroatoms selected from oxygen, sulfur and nitrogen.

Typical examples thereof include an indanyl group, a 1,2,3,4-tetrahydronaphth-1-yl or -2-yl group, a 5,6,7,8-tetrahydroquinoline-5-yl, -6-yl, -7-yl or -8-yl group, a 5,6,7,8-tetrahydroisoquinoline-5-yl, -6-yl, -7-yl or -8-yl group, a 4,5,6,7-tetrahydrobenzothiophene-4-yl, -5-yl, -6-yl or -7-yl group, a dibenzo [2,3,6,7] cycloheptan-1-yl or -4-yl group, a dibenzo [2,3,6,7] cyclohept-4-ene-1-yl or -4-yl group, or a 9-fluorenyl group Examples of the "non-aromatic heterocyclic ring being condensed with 1 or 2 aromatic hydrocarbon rings or aromatic heterocyclic rings" includes a group wherein a non-aromatic 4- to 7-membered cyclic group containing 1 or 2 heteroatoms selected from oxygen, sulfur and nitrogen has been condensed with a benzene ring or with an aromatic 5- to 6-memberred ring containing 1 to 4 heteroatoms selected from oxygen, sulfur and nitrogen.

Typical examples thereof include a 2,3-dihydrobenzopyran-2-yl, -3-yl or -4-yl group, a xanthene-9-yl, 1,2,3,4-tetrahydroquinoline-1-yl, -2-yl, -3-yl or 4-yl, a 9,10-dihydroacridine-9-yl or -10-yl group, a 2,3-dihydrobenzothiopyran-2-yl, -3-yl or -4-yl group, or a dibenzothiopyran-4-yl group.

The "thioalkyl" group include a thio($C_1$–$C_8$)alkyl group.

The group $R^1$ in the 2-oxobicyclo[3.1.0]hexane-6-carboxylate of formula of the present invention will be explained below.

Examples of the $C_1$ to $C_{10}$ alkyl group which may be substituted with at least one group selected from a $C_1$ to $C_8$ alkoxy, halogen or nitro, for example, include a methyl group, ethyl group, n-propyl group, isopropyl group, n-butyl group, isobutyl group, see-butyl group, t-butyl group, n-pentyl group, isopentyl group, neopentyl group, n-hexyl group, n-heptyl group, n-octyl group, cyclohexyl group and cycloheptyl group.

Examples of the arylalkyl group, which aryl may be substituted with at least one group selected from a $C_1$ to $C_8$ alkyl, $C_1$ to $C_8$ alkoxy, halogen or nitro, for example, include a benzyl group, 4-chlorobenzyl group, 4methoxybenzyl group, 4-nitrobenzyl group, 4-methylbenzyl group, 2,4-dimethoxybenzyl group, 2,4,6-trimethylbenzyl group, α-phenylethyl group, β-phenylethyl group, phenylpropyl group, benzhydryl group and triphenylmethyl group.

Examples of the aryl group which may be substituted with at least one group selected from a $C_1$ to $C_8$ alkyl, $C_1$ to $C_8$ alkoxy, halogen or nitro on the aromatic ring thereof, for example, include a phenyl group, 4-methylphenyl group, 4-chlorophenyl group, 4-methoxyphenyl group, 4-nitrophenyl group and 2-naphthyl group.

Preferable examples thereof include a $C_1$ to $C_5$ alkyl group such as methyl group, ethyl group, propyl group, isopropyl group, n-butyl group, isobutyl group, sec-butyl group, t-butyl group, n-pentyl group, isopentyl group and neopentyl group, an allyl group, a benzyl group which may be substituted with at least one group selected from a halogen atom or a ($C_1$–$C_4$)alkoxy group, on its aromatic ring, such as 4chlorobenzyl group etc., and a phenyl group which may be substituted with at least one group on its aromatic ring, for example, 4methylphenyl group etc.

More preferable examples include a $C_1$ to $C_4$ alkyl group such as methyl group, ethyl group, propyl group, n-butyl group or isobutyl group.

The examples of $R^1$ may have asymmetric carbon atom (s).

In the 2-oxobicyclo[3.1.0]hexane-6-carboxylates of formula (1) used in the method of the present invention, $X^1$ and $X^2$ include a single bond, S, SO, $SO_2$, NH and NHCO, among which a single bond is preferred.

$R^2$ and $R^3$ in the 2-oxobicyclo[3.1.0]hexane-6-carboxylates of formula (1) used in the method of the present invention will be explained below.

Examples of $R^2$ and $R^3$ include e.g. a hydrogen atom, a halogen atom or a nitro group.

Examples of the $C_1$ to $C_{10}$ alkyl group which may be substituted with at least one group selected from a $C_1$ to $C_8$ alkoxy, hydroxy, halogen, amino, nitro, thiol or thioalkyl, for example, include a methyl group, ethyl group, n-propyl group, isopropyl group, n-butyl group, isobutyl group, sec-butyl group, t-butyl group, n-pentyl group, isopentyl group, neopentyl group, n-hexyl group, n-heptyl group, n-octyl group, cyclohexyl group and cycloheptyl group.

Examples of the $C_2$ to $C_{10}$ alkenyl group which may be substituted with at least one group selected from a $C_1$ to $C_8$ alkoxy, hydroxy, halogen, amino, nitro, thiol or thioalkyl include, for example, an allyl group.

Examples of the $C_2$ to $C_{10}$ alkynyl group which may be substituted with at least one group selected from a $C_1$ to $C_8$ alkoxy, hydroxy, halogen, amino, nitro, thiol or thioalkyl, for example, a propynyl group.

Examples of the aryl group which may be substituted with at least one group selected from a $C_1$ to $C_8$ alkyl, $C_1$ to $C_8$ alkoxy, hydroxy, halogen, amino, nitro, thiol, thioalkyl or phenyl on the aromatic ring thereof include, for example, 2-naphthyl group, phenyl group, 2-fluorophenyl group, 3-fluorophenyl group, 4-fluorophenyl group, 3,4-difluorophenyl group, pentafluorophenyl group, 2-chlorophenyl group, 3-chlorophenyl group, 4-chlorophenyl group, 3,4-dichlorophenyl group, 2,5-dichlorophenyl group, 2-bromophenyl group, 3-bromophenyl group, 4-bromophenyl group, 2-methylphenyl group, 3-methylphenyl group, 4-methylphenyl group, 2-methoxyphenyl group, 3-methoxyphenyl group, 4-methoxyphenyl group, and 4-nitrophenyl group.

Examples of the arylalkyl group which may be substituted with at least one group selected from a $C_1$ to $C_8$ alkyl, $C_1$ to $C_8$ alkoxy, hydroxy, halogen, amino, nitro, thiol, thioalkyl or phenyl on the aromatic Ling thereof include, for example, a benzyl group, 2-fluorobenzyl group, 3-fluorobenzyl group, 4-fluorobenzyl group, 2,3-difluorobenzyl group, 2,4-difluorobenzyl group, 2,5-difluorobenzyl group, 3,5-difluorobenzyl group, 3,4-difluorobenzyl group, 2,3,4-trifluorobenzyl group, 2-chlorobenzyl group, 3-chlorobenzyl group, 4chlorobenzyl group, 2,3-dichlorobenzyl group, 3-chloro-4-fluorobenzyl group, 2-methylbenzyl group, 3-methylbenzyl group, 4-methylbenzyl group, 4-fluoro-3-methylbenzyl group, 3-fluoro-2-methylbenzyl group, 3,5-dimethylbenzyl group, 4-isopropylbenzyl group, 2,4-dimethylbenzyl group, 2,5-dimethylbenzyl group, 2,4,6-trimethylbenzyl group, 2-methoxybenzyl group, 3-methoxybenzyl group, 4-methoxybenzyl group, 2,4-dimethoxybenzyl group, 3-fluoro-4-methoxybenzyl group, 3-methyl-4-methoxybenzyl group, 4-phenlylbenzyl group, 4-nitrobenzyl group, α-phenylethyl group, β-phenylethyl group, phenylpropyl group, benzhydryl group and triphenylmethyl group.

Examples of the aromatic heterocyclic group which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl, include, for example, a 2-pyrimidyl group.

Examples of the non-aromatic heterocyclic group which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl, include, for example, an azetidine-1-yl group, an azetidine-2-yl group, pyrrolidine-2-yl group and piperidine-3-yl group.

Examples of the non-aromatic hydrocarbon cyclic group condensed with 1 or 2 aromatic hydrocarbon rings or aromatic heterocyclic rings, which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl, include, for example, an indanyl group and a 1,2,3,4-tetrahydronaphtho-1-yl group.

Examples of the non-aromatic heterocyclic group condensed with 1 or 2 aromatic hydrocarbon rings or aromatic heterocyclic rings, which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl, include, for example, 2,3-dihydrobenzopyran-2-yl and xanthene-9-yl.

Preferable groups for $R^2$ and $R^3$ are a hydrogen atom, halogen atom, nitro group, methyl group or allyl group, and a hydrogen atom is more preferred.

Examples of the 2-oxobicyclo[3.1.0]hexane-6-carboxylates of formula (1) include e.g. methyl 2-oxobicyclo[3.1.0]hexane-6-carboxylate, ethyl 2-oxobicyclo[3.1.0]hexane-6-carboxylate, n-propyl 2-oxobicyclo[3.1.0]hexane-6-carboxylate, isopropyl 2-oxobicyclo[3.1.0]hexane-6-carboxylate, n-butyl 2-oxobicyclo[3.1.0]hexane-6-carboxylate, isobutyl 2-oxobicyclo[3.1.0]hexane-6-carboxylate, sec-butyl 2-oxobicyclo[3.1.0]hexane-6-carboxylate, t-butyl 2-oxobicyclo[3.1.0]hexane-6-carboxylate, n-pentyl 2-oxobicyclo[3.1.0]hexane-6-carboxylate, isopentyl 2-oxobicyclo[3.1.0]hexane-6-carboxylate, neopentyl 2-oxobicyclo[3.1.0]hexane-6-carboxylate, n-hexyl 2-oxobicyclo[3.1.0]hexane-6-carboxylate, cyclohexyl 2-oxobicyclo[3.1.0]hexane-6-carboxylate, n-heptyl 2-oxobicyclo[3.1.0]hexane-6-carboxylate, cycloheptyl 2-oxobicyclo[3.1.0]hexane-6-carboxylate, n-octyl 2-oxobicyclo[3.1.0]hexane-6-carboxylate, allyl 2-oxobicyclo[3.1.0]hexane-6-carboxylate, benzyl 2-oxobicyclo[3.1.0]hexane-6-carboxylate, 4-chlorobenzyl 2-oxobicyclo[3.1.0]hexane-6-carboxylate, 4-methoxybenzyl 2-oxobicyclo [3.1.0]hexane-6carboxylate, 4-nitrobenzyl 2-oxobicyclo[3.1.0]hexane-6-carboxylate, 4-methylbenzyl 2-oxobicyclo[3.1.0]hexane-6-carboxylate, 2,4-dimethoxybenzyl 2-oxobicyclo[3.1.0]hexane-6-carboxylate, 2,4,6-trimethylbenzyl 2-oxobicyclo[3.1.0]hexane-6-carboxylate, (S)-phenylethyl 2-oxobicyclo[3.1.0]hexane-6-carboxylate, (R)-phenylethyl 2-oxobicyclo[3.1.0]hexane-6-carboxylate, β-phenylethyl 2-oxobicyclo[3.1.0]hexane-6-carboxylate, phenylpropyl 2-oxobicyclo[3.1.0]hexane-6-carboxylate, benzhydryl 2-oxobicyclo[3.1.0]hexane-6-carboxylate, triphenylmethyl 2-oxobicyclo[3.1.0]hexane-6-carboxylate, phenyl 2-oxobicyclo[3.1.0]hexane-6-carboxylate, 4-methylphenyl 2-oxobicyclo[3.1.0]hexane-6-carboxylate, 4-chlorophenyl 2-oxobicyclo[3.1.0]hexane-6-carboxylate, 4-methoxyphenyl 2-oxobicyclo[3.1.0]hexane-6-carboxylate, 4-nitrophenyl 2-oxobicyclo[3.1.0]hexane-6-carboxylate, 2-naphthyl 2-oxobicyclo[3.1.0]hexane-6-carboxylate, and compounds which are further substituted at the 3- and 4-positions in the above-described compounds independently with at least one group selected from a halogen atom, a nitro group, methyl group, ethyl group, n-propyl group, isopropyl group, n-butyl group, isobutyl group, sec-butyl group, t-butyl group, n-pentyl group, isopentyl group, neopentyl group, n-hexyl group, n-heptyl group, n-octyl group, cyclohexyl group, cycloheptyl group, allyl group, propynyl group, 2-naphthyl group, phenyl group, 2-fluorophenyl group, 3-fluorophenyl group, 4-fluorophenyl group, 3,4-difluorophenyl group, pentafluorophenyl group, 2-chlorophenyl group, 3-chlorophenyl group, 4-chlorophenyl group, 3,4-dichlorophenyl group, 2,5-dichlorophenyl group, 2-bromophenyl group, 3-bromophenyl group, 4-bromophenyl group, 2-methylphenyl group, 3-methylphenyl group, 4-methylphenyl group, 2-methoxyphenyl group, 3-methoxyphenyl group, 4-methoxyphenyl group,
4-nitrophenyl group, benzyl group, 2-fluorobenzyl group,
3-fluorobenzyl group, 4-fluorobenzyl group, 2,3-difluorobenzyl group,
2,4-difluorobenzyl group, 2,5-difluorobenzyl group, 3,6-difluorobenzyl group,
3,4-difluorobenzyl group, 2,3,4-trifluorobenzyl group, 2-chlorobenzyl group,
3-chlorobenzyl group, 4-chlorobenzyl group, 2,3-dichlorobenzyl group,
3-chloro-4-fluorobenzyl group, 2-methylbenzyl group, 3-methylbenzyl group,
4methylbenzyl group, 4-fluoro3-methylbenzyl group, 3-fluoro-2-methylbenzyl group, 3,5-dimethylbenzyl group, 4-isopropylbenzyl group,
2,4-dimethylbenzyl group, 2,5-dimethylbenzyl group, 2,4,6-trimethylbenzyl group, 2-methoxybenzyl group,
3-methoxybenzyl group, 4-methoxybenzyl group, 2,4-dimethoxybenzyl group,
3-fluoro-4methoxybenzyl group, 3-methyl-4-methoxybenzyl group,
4-phenylbenzyl group, 3-phenoxybenzyl group,
4-nitrobenzyl group, α-phenylethyl group, 2-phenylethyl group,
phenylpropyl group, benzhydryl group, triphenylmethyl group,
2-pyrimidyl group,
azetidine-1-yl group, azetidine-2-yl group, pyrrolidine-2-yl group,
piperidine-3-yl group, indanyl group, 1,2,3,4-tetrahydronaphtho-1-yl group,
2,3-dihydrobenzopyran-2-yl group and xanthene-9-yl group.

Examples of preferable compounds thereof include
methyl 2-oxobicyclo[3.1.0]hexane-6-carboxylate,
ethyl 2-oxobicyclo[3.1.0]hexane-6-carboxylate,
n-propyl 2-oxobicyclo[3.1.0]hexane-6-carboxylate,
isopropyl 2-oxobicyclo[3.1.0]hexane-6-carboxylate,
n-butyl 2-oxobicyclo[3.1.0]hexane-6-carboxylate,
isobutyl 2-oxobicyclo[3.1.0]hexane-6-carboxylate,
sec-butyl 2-oxobicyclo[3.1.0]hexane-6-carboxylate,
t-butyl 2-oxobicyclo[3.1.0]hexane-6-carboxylate,
n-pentyl 2-oxobicyclo[3.1.0]hexane-6-carboxylate,
isopentyl 2-oxobicyclo[3.1.0]hexane-6-carboxylate,
neopentyl 2-oxobicyclo[3.1.0]hexane-6-carboxylate,
allyl 2-oxobicyclo[3.1.0]hexane-6-carboxylate,
benzyl 2-oxobicyclo[3.1.0]hexane-6-carboxylate,
4-chlorobenzyl 2-oxobicyclo[3.1.0]hexane-6-carboxylate,
4-methoxybenzyl 2-oxobicyclo[3.1.0]hexane-6-carboxylate,
4-nitrobenzyl 2-oxobicyclo[3.1.0]hexane-6-carboxylate,
4-methylbenzyl 2-oxobicyclo[3.1.0]hexane-6-carboxylate, 2,4-dimethoxybenzyl 2-oxobicyclo[3.1.0]hexane-6-carboxylate,
2,4,6-trimethylbenzyl 2-oxobicyclo[3.1.0]hexane-6-carboxylate,
phenyl 2-oxobicyclo[3.1.0]hexane-6-carboxylate,
4-methylphenyl 2-oxobicyclo[3.1.0]hexane-6-carboxylate,
4-chlorophenyl 2-oxobicyclo[3.1.0]hexane-6-carboxylate,
4-methoxyphenyl 2-oxobicyclo[3.1.0]hexane-6-carboxylate,
4-nitrophenyl 2-oxobicyclo[3.1.0]hexane-6-carboxylate, and compounds
which are further substituted at the 3- and 4-positions in the above-described compounds independently with a halogen atom, a nitro group, methyl group or allyl group.

More preferable compounds thereof include
methyl 2-oxobicyclo[3.1.0]hexane-6-carboxylate,
ethyl 2oxobicyclo[3.1.0]hexane-6-carboxylate,
n-propyl 2-oxobicyclo[3.1.0]hexane-6-carboxylate,
isopropyl 2-oxobicyclo[3.1.0]hexane-6-carboxylate,
n-butyl 2-oxobicyclo[3.1.0]hexane-6-carboxylate,
isobutyl 2-oxobicyclo[3.1.0]hexane-6-carboxylate,
sec-butyl 2-oxobicyclo[3.1.0]hexane-6-carboxylate and
t-butyl 2-oxobicyclo[3.1.0]hexane-6-carboxylate.

The enzyme (referred to hereinafter as the present enzyme) having an ability to asymmetrically hydrolyze 2-oxobicyclo[3.1.0]hexane-6-carboxylate of formula (1) which can be used in the present invention may be either an enzyme derived from microorganisms or an enzyme from animals.

Examples of the present enzyme derived from microorganisms includes e.g. a hydrolase derived from microorganisms such as the genus Achromobacter, Alcaligenes, Arthrobacter, Aspergillus, Bacillus, Burkholderia, Candida, Chromobacterium, Humicola, Mucor, Pseudomonas or Rhizomucor. Enzymes derived from Arthrobacter, Aspergillus, Bacillus, Burkholderia, Candida, Chromobacterium, Humicola and Pseudomonas are preferred. Enzyme from the genus Bacillus, Candida, Chromobacterium and Pseudomonas are particularly preferred.

Examples of the present enzyme include
mutant enzymes derived from these microorganisms as described above by treatment with a mutagen or UV rays,
enzymes produced by a recombinant microorganism transformed by introducing a gene coding for the present enzyme into the microorganism,
mutant enzymes of the present enzyme wherein one or more specific amino acids have been deleted, added or replaced by genetic engineering techniques, and any enzymes with the ability to asymmetrically hydrolyze 2-oxobicyclo[3.1.0]hexane-6-carboxylates of formula (1).

Specifically, examples of the present enzyme include
an enzyme derived from the microorganism *Aspergillus melleus, Aspergillus oryzae, Backfills licheniformis, Bacillus subtilis, Bacillus thermoglueosidasius, Burkholderia cepacia, Candida antarctica, Candida cylindracea, Candida rugosa, Chromobacterium viscosum, Mucor miehei, Pseudomonas aeruginosa, Pseudomonas cepacia, Pseudomonas fluorescens*or *Rhizomucor miehei*, and those from Chromobacterium SC-YM-1 (FERM BP-6703 transferred from FERM P-14009), Arthrobacter SC-6-98-28 (FERM BP-3658) or Burkholderia cepacia SC-20.

Eenzymes derived from *Aspergillus oryzae, Bacillus thermoglucosidasius, Burkholderia cepacia, Candida antarctica, Candida cylindracea, Candida rugosa* or *Pseudomonas aeruginosa*, or from Chromobacterium SC-YM-1 (FERM BP-6703 transferred from FERM P-14009), Arthrobacter SC-6-98-28 (FERM BP-3658) or *Burkholderia cepacia* SC-20(FERM BP-5740) are preferred.

Particularly preferred are enzymes derived from *Bacillus thermoglucosidasius, Candida antarctica, Candida cylindracea*, Chromobacterium SC-YM-1 (FERM BP-6703 transferred from FERM P-14009).

The method of preparing a recombinant microorganism transformed by introducing a gene coding for the present enzyme into the microorganism includes usual genetic engineering techniques according to e.g. J. Sambrook, E. P. Fritsch, T. Maniatis: Molecular Cloning 2nd edition, Cold Spring Harbor Laboratory (1989). More specific examples include methods according to those described in JP-A 7-163364, JP-A 5-56787 or JP-A 10-210975.

Specific examples of the present enzyme produced by recombinant microorganisms include an esterase derived from Arthrobacter SC-6-98-28 (FERM BP-3658) (JP-A 5-56787), an esterase derived from Chromobacterium SC-YM-1 (FE1M BP-6703 transferred from FERM P-14009) (JP-A 7-163364) or a lipase derived from *Burkholderia cepacia* SC-20 (JP-A 10-210975).

The method of preparing the mutant enzyme by genetic engineering techniques includes e.g. the method of Olfert Landt et al. (Genes 96, 125–128, 1990). More specific examples include a method according to that described in JP-A 7-213280.

Specific examples of the mutant enzyme include a mutant esterase or lipase which is prepared from an esterase derived from Chromobacterium SC-YM-1, an esterase derived from Arthrobacter SC-6-98-28 (BERM BP-3658) or a lipase derived from *Burkholderia cepacia*.

Any microorganisms producing the present enzyme can be cultured in a usual manner in a liquid medium. The medium used may be any kind of medium suitably containing a carbon source, a nitrogen source, inorganic materials used in usual culture of microorganisms. For example, the carbon source includes glucose, glycerin, organic acids, molasses etc.

The nitrogen source includes peptone, yeast extract, malt extract, soybean powder, corn steep liquor, cotton seed powder, dried yeast, casamino acid, ammonium chloride, ammonium nitrate, ammonium sulfate, urea etc.

The inorganic materials include salts, sulfates and phosphates of potassium, sodium, magnesium, iron, manganese, cobalt, zinc etc., and specifically, it is possible to use potassium chloride, sodium chloride, magnesium sulfate, ferrous sulfate, manganese sulfate, cobalt chloride, zinc sulfate, potassium phosphate and sodium phosphate.

Further, triglyceride such as olive oil or tributyrin or 2-oxobicyclo[3.1.0]hexane-6-carboxylates of formula (1) may be added to the medium, if necessary, in order to raise the ability of the above-described microorganisms to asymmetrically hydrolyze 2-oxobicyclo[3.1.0]hexane-6-carboxylates of formula (1).

Culture is conducted usually aerobically, and shake culture or aeration stirring culture is preferable. The culture temperature is usually about 20 to 40° C., preferably about 25 to 35° C., and the pH value is preferably about 6 to 8. Though varying depending on conditions, the culture time is preferably about 1 to 7 days.

Further, a method of culture on solid medium can also be adopted, if necessary, insofar as the microorganism having the ability to asymmetrically hydrolyze 2-oxobicyclo[3.1.0] hexane-6-carboxylates of formula (1) can be obtained.

Purification of the present enzyme from a culture of the microorganism cultured in the manner described above may be conducted by a usual method used in purification of enzymes. For example, the microorganism in the microbial culture is first disrupted by sonication or with a dynomill or a French press. From the resulting solution after disruption, insolubles are removed by e.g. centrifugation, and the desired enzyme can be purified from the supernatant by cation-exchange column chromatography, anion-exchange column chromatography, hydrophobic column chromatography or gel filtration column chromatography or by a suitable combination thereof Examples of carriers used in these column chromatographic techniques include DEAE-Sepharose fastflow (Amersham Pharmacia Biotech) and Butyl-Toyopearl 650S (Tosoh Corporation).

Examples of the present enzyme derived from animals includes an enzyme derived from porcine internal organs, bovine internal organs or sheep internal organs, more specifically a hydrolase derived from the porcine kidney or bovine pancreas.

Commercial enzyme can also be used in the present invention. Examples of commercial enzymes that can be used as the present enzyme include e.g.

cholesterol esterase (derived from *Candida mimosa*),

Chirazyme E-3 (derived from thermophilic bacteria),

Chirazyme E-4 (derived from thermophilic bacteria),

Chirazyme E-5 & Chirazyme L-2 (derived from *Candida antarctica*),

Chirazyme L-5 (derived from *Candida antarctica*),

Chirazyme L-6 (derived from *Pseudomonas cepacia*),

Chirazyme L-8 (derived Humicola sp.),

Chirazyme L-9 (derived from *Mucor miehei*),

Chirazyme L-10(derived from Alcaligenes sp.) and

Chirazyme P-1 (derived from *Bacillus licheniformis*), all of which are products of Roche Diagnostics, Lipase OF (derived from *Candida cylindracea*), Lipase AL (derived from Achromobacter sp.), Lipase QL (derived from Acaligenes sp.) and Lipase PL (derived from Alcaligenes sp.), all of which are products of Meito Sangyo K.K., Toyozyme (derived from *Pseudomonas aeruginosa*), which is a product of (Toyobo Co., Ltd.), Protease P (derived from *Aspergillus melleus*), Protease N (derived from *Bacillus subtilis*), Prolazer (derived from Bacillus sp.), Lipase AH (derived from *Pseudomonas cepacia*) and Lipase AK (derived from

*Pseudomonas fluorescing*), all of which are products of Amano Pharmaceutical Co., Ltd., Liposam (derived from Pseudomonas sp.), which is a product of Showa Denko, K.K., lipase (derived from *Chromobacterium viscosum*), which is a product of Asahi Chemical Co., Ltd., α-chymotrypsin (derived from bovine pancreas), γ-chymotrypsin (derived from bovine pancreas) and δ-chymotrypsin (derived from bovine pancreas), all of which are products of Sigma Company, Limited, lipase (derived from *Mucor miehei*), which is a product of Biocatalysts Ltd., Esterase 46054 (derived from *Bacillus thermoglucosidasius*), Lipase 62285 (derived from *Aspergillus oryzae*) and Lipase 62291 (derived from *Rhizomucor miehei*), all of which are products of Fluka Company, Limited, Kitopearl Cholesterol Esterase CEN (derived from Pseudomonas sp.), Kitopearl Lipase AP (derived from bacteria) and Kitopearl Lipase CV (derived from *Chromobacterium viscosum*), all of which are products of Fuji Spinning Co., Ltd., cholesterol esterase (derived from Pseudomonas sp.), lipase (derived from Pseudomonas sp.) and Acylase I (derived from porcine kidney), all of which are products of Wako Pure Chemical Industries, Ltd.

Preferable examples thereof include cholesterol esterase (derived from *Candida rugosa*), Chirazyme E-3 (derived from thermophilic bacteria), Chirazyme E-4 (derived from thermophilic bacteria), Chirazyme E-5 (derived from thermophilic bacteria), Chirazyme L-2 (derived from *Candida antarctica*), Chirazyme L-5 (derived from *Candida antarctica*), Chirazyme L-6 (derived from Pseudomonas cepacia) and Chirazyme L-8 (derived Humicola sp.), all of which are products of Roche Diagnostics, Lipase OF (derived from *Candida cylindracea*), which is a product of Meito Sangyo K. K., Toyozyme (derived from *Pseudomonas aeruginosa*) (Toyobo Co., Ltd.), Liposam (derived from Pseudomonas sp.) (Showa Denko, K. K.), Esterase 46054 (derived from *Bacillus thermoglucosidasius*) and Lipase 62285 (derived from *Aspergillus oryzae*), both of which are products of Fluka, and cholesterol esterase (derived from Pseudomonas sp.) and lipase (derived from Pseudomonas sp.), all of which are products of Wako Pure Chemical Com, Ltd.).

Particularly preferable examples thereof include

Chirazyme E-4 (derived from thermophilic bacteria), Chirazyme L-5 (derived from *Candida antarctica*) and Chirazyme L-6 (derived from *Pseudomonas cepacia*) (which are products of Roche Diagnostics), Lipase OF (derived from *Candida cylindracea*) (The Meito Sangyo K.K.), and Esterase 46054 (derived from *Bacillus thermoglucosidasius*) (Fluka).

The present enzyme may be used in various forms such as purified enzyme, crude enzyme, microbial culture, microorganisms themselves and treated materials thereof. The treated materials refer to lyophilized microorganisms, acetone-dried microorganisms, disrupted microorganisms, autolyzed microorganisms, sonicated microorganisms, extracts from the microorganisms and alkali-treated materials of microorganisms.

Further, the enzyme with various degrees of purity or in various forms described above may be immobilized by known techniques such as a method of adsorption onto inorganic carriers (silica gel, ceramics etc.), cellulose or ion-exchange resin, a polyacrylamide method, a sulfuric polysaccharide-gel method (e.g. carrageenan-gel method), an alginic acid-gel method and an agar-gel method.

From these enzymes described above, the enzyme may be suitably selected depending on the desired optically active 2-oxobicyclo[3.1.0]hexane-6-carboxylate of formula (3) or the desired optically active 2-oxobicyclo[3.1.0]hexane-6-carboxylic acids of formula (2). The amount of the enzyme is suitably set so as not to permit a delay in the reaction or a reduction in selectivity. For example, when the purified or crude enzyme or the commercial enzyme is used, the amount of the enzyme used is usually 0.001 to 2 parts by weight, preferably 0.002 to 0.5 part by weight per 1 part by weight of the 2-oxobicyclo[3.1.0]hexane-6-carboxylates of formula (1), and when the culture of the microorganisms, the microorganisms themselves or treated materials thereof are used, the amount of such materials is usually about 0.01 to 200 parts by weight, preferably about 0.1 to 50 parts by weight per 1 part by weight of the 2-oxobicyclo[3.1.0]hexane-6-carboxylates of formula (1).

Water may be used in the asymmetric hydrolysis reaction and may be an aqueous buffer. The aqueous buffer includes e.g. aqueous buffers of inorganic salts such as aqueous alkali-metal phosphates, for example aqueous sodium phosphate and aqueous potassium phosphate, and aqueous buffers of organic acid salts such as alkali-metal acetates, for example aqueous sodium acetate and aqueous potassium acetate. The amount of water used in such buffers may be usually 0.5 mole or more (or usually not more than 200 parts by weight) per 1 mol of 2-oxobicyclo[3.1.0]hexane-6-carboxylates of formula (1), or may be used as a solvent.

The asymmetrical hydrolysis reaction may be conducted in the presence of organic solvent such as hydrophobic organic solvent or hydrophilic organic solvent. Such organic solvent is used preferably for improving the optical purity of the optically active 2oxobicyclo[3.1.0]hexane-6-carboxylate of formula (3a) or (3b) and the optically active 2-oxobicyclo[3.1.0]hexane-6-carboxylic acids of formula (2a) or (2b).

The hydrophobic organic solvent includes e.g. ethers such as t-butyl methyl ether, isopropyl ether and hydrocarbons such as toluene, hexane, cyclohexane, heptane, octane and isooctane, and the hydrophilic organic solvent includes e.g. alcohols such as t-butanol, methanol, ethanol, isopropanol, isobutanol and n-butanol, ethers such as tetrahydrofuran, sulfoxides such as dimethyl sulfoxide, ketones such as acetone, nitrites such as acetonitrile, and amides such as N,N-dimethylformamide. These hydrophobic or hydrophilic organic solvents are used alone or in combination thereof, and the hydrophobic organic solvent and the hydrophilic organic solvent may be used in combination.

If such organic solvent is used, the weight of the solvent used is usually not more than 200 parts by weight, preferably about 0.1 to 100 parts by weight per 1 part by weight of 2-oxobicyclo[3.1.0]hexane-6-carboxylate of formula (1).

The asymmetric hydrolysis reaction is conducted by a method in which e.g. water, 2-oxobicyclo[3.1.0]hexane-6-carboxylate of formula (1), and the present enzyme are mixed with one another, and when the organic solvent is used, the organic solvent, water, 2-oxobicyclo[3.1.0]hexane-6carboxylate of formula (1) and the present enzyme may be mixed with one another.

The pH value in the reaction system, which is usually in the range of about pH 4 to 10, is selected suitably without particular limitation so that asymmetrical hydrolysis proceeds selectively with the present enzyme.

The reaction temperature is usually in the range of about 5 to 65° C., preferably about 20 to 50° C., because a too high reaction temperature tends to lower the stability of the enzyme, while a too low temperature causes a reduction in the reaction rate.

Thus, the optically active 2-oxobicyclo[3.1.0]hexane-6-carboxylate of formula (1) are hydrolyzed selectively while maintaining the steric configuration around the asymmetric carbon atoms at 1-, 5- and 6-positions, to form the desired optically active 2-oxobicyclo[3.1.0]hexane-6-carboxylic acid of formula (2a) or (2b).

The reaction mixture after completion of the reaction is separated into aqueous and organic layers to give an aqueous solution of the optically active 2-oxobicyclo[3.1.0]hexane- 6-carboxylic acid of formula (2a) or (2b). When the hydrophobic organic solvent is used in the enzymatic hydrolysis, the resulting reaction mixture can be separated by phase separation as such: However, if no or little hydrophobic organic solvent is used in the hydrolysis reaction or when the amount of water used is not enough for the phase separation of the product, then the product may be separated after the hydrophobic organic solvent or water is added, if necessary.

The hydrophobic organic solvent includes e.g. ethers such as t-butyl methyl ether and isopropyl ether, hydrocarbons such as toluene, hexane, cyclohexane, heptane, octane and isooctane, halogenated hydrocarbons such as dichloromethane, dichloroethane, chloroform, chlorobenzene and o-dichlorobenzene and esters such as ethyl acetate, methyl acetate and butyl acetate.

Then, the water may be distilled off from the resulting aqueous solution of the optically active 2-oxobicyclo[3.1.0]hexane-6-carboxylic acid of formula (2a) or (2b) whereby the desired optically active 2-oxobicyclo[3.1.0]hexane-6-carboxylic acids of formula (2a) or (2b) can be recovered. Alternatively, after an acid is added to the reaction solution, the product is extracted with a suitable organic solvent, and the organic solvent is distilled off whereby the product can also be recovered and separated. The obtained optically active 2-oxobicyclo[3.1.0]hexane-6-carboxylic acid of formula (2a) or (2b) may be further purified by e.g. recrystallization and/or column chromatography.

Specific examples of thus obtained optically active 2-oxobicylo[3.1.0]hexane-6-carboxylic acid of formula (2) includes e.g. (+)-(1S,5R,6S)-2-oxobicyclo[3.1.0]hexane-6-carboxylic acid and (−)-(1R,5S,6R)-2-oxobicyclo[3.1.0]hexane-6-carboxylic acid, and compounds which are further substituted at the 3- and 4-positions independently with at least one group selected from
a halogen atom, a nitro group,
a methyl, ethyl, n-propyl, isopropyl, n-butyl, isobutyl, sec-butyl, t-butyl, n-pentyl, isopentyl, neopentyl, n-hexyl, n-heptyl, n-octyl, cyclohexyl, and cycloheptyl group,
an allyl group,
a propynyl group,
a 2-naphthyl group, phenyl group, 2-fluorophenyl group, 3-fluorophenyl group, 4-fluorophenyl group, 3,4-difluorophenyl group, pentafluorophenyl group, 2-chlorophenyl group, 3-chlorophenyl group, 4-chlorophenyl group, 3,4-dichlorophenyl group, 2,5-dichlorophenyl group, 2-bromophenyl group, 3-bromophenyl group, 4-bromophenyl group, 2-methylphenyl group, 3-methylphenyl group, 4-methylphenyl group, 2-methoxyphenyl group, 3-methoxyphenyl group, 4-methoxyphenyl group, 4-nitrophenyl group, benzyl group, 2-fluorobenzyl group, 3-fluorobenzyl group, 4-fluorobenzyl group, 2,3-difluorobenzyl group, 2,4-difluorobenzyl group, 2,5-difluorobenzyl group, 3,5-difluorobenzyl group, 3,4-difluorobenzyl group, 2,3,4-trifluorobenzyl group, 2-chlorobenzyl group, 3-chlorobenzyl group, 4-chlorobenzyl group, 2,3-dichlorobenzyl group, 3-chloro-4-fluorobenzyl group, 2-methylbenzyl group, 3-methylbenzyl group, 4-methylbenzyl group, 4-fluoro-3-methylbenzyl group, 3-fluoro-2-methylbenzyl group, 3,5-dimethylbenzyl group, 4-isopropylbenzyl group, 2,4-dimethylbenzyl group, 2,5-dimethylbenzyl group, 2,4,6-trimethylbenzyl group, 2-methoxybenzyl group, 3-methoxybenzyl group, 4-methoxybenzyl group, 2,4-dimethoxybenzyl group, 3-fluoro-4-methoxybenzyl group, 3-methyl-4-methoxybenzyl group, 4-phenylbenzyl group, 4-nitrobenzyl group, α-phenylethyl group, β-phenylethyl group, phenylpropyl group, benzhydryl group, triphenylmethyl group,
a 2-pyrimidyl group,
an azetidine-1-yl azetidine-2-yl, pyrrolidine-2-yl, and piperidine-3-yl group, and
an indanyl, 1,2,3,4-tetrahydronaphth-1-yl, 2,3-dihydrobenzopyran-2-yl and xanthene-9-yl group.

Then, the other enantiomer ester that has not been hydrolyzed by the enzyme, such as the 2-oxobicyclo[3.1.0]hexane-6-carboxylate of formula (3a) or (3b) is contained in an organic layer after phase separation, and this product can be easily recovered from the organic layer for example by distilling the solvent off. The resulting optically active 2-oxobicyclo[3.1.0]hexane-6-carboxylate of formula (3a) or (3b) may be further purified by recrystallization and/or column chromatography.

Thus obtained optically active 2-oxobicyclo[3.1.0]hexane-6-carboxylate of formula (3) includes e.g.

methyl(1S,5R,6S)-2-oxobicyclo[3.1.0]hexane-6-carboxylate,
ethyl(1S,5R,6S)-2-oxobicyclo[3.1.0]hexane-6-carboxylate,
n-propyl(1S,5R,6S)-2-oxobicyclo[3.1.0]hexane-6-carboxylate,
isopropyl(1S,5R,6S)-2-oxobicyclo[3.1.0]hexane-6-carboxylate,
n-butyl(1S,5R,6S)-2-oxobicyclo[3.1.0]hexane6-carboxylate,
isobutyl(1S,5R,6S)-2-oxobicyclo[3.1.0]hexane-6-carboxylate,
sec-butyl(1S,5R,6S)-2-oxobicyclo[3.1.0]hexane-6-carboxylate,
t-butyl(1S,5R,6S)-2-oxobicyclo[3.1.0]hexane-6-carboxylate,
n-pentyl(1S,5R,6S)-2-oxobicyclo[3.1.0]hexane-6-carboxylate,
isopentyl(1S,5R,6S)-2-oxobicyclo[3.1.0]hexane-6-carboxylate,
neopentyl(1S,5R,6S)-2-oxobicyclo[3.1.0]hexane-6-carboxylate,
n-hexyl(1S,5R,6S)-2-oxobicyclo[3.1.0]hexane-6-carboxylate,
cyclohexyl(1S,5R,6S)-2-oxobicyclo[3.1.0]hexane-6-carboxylate,
n-heptyl(1S,5R,6S)-2-oxobicyclo[3.1.0]hexane-6-carboxylate,
cycloheptyl(1S,5R,6S)-2-oxobicyclo[3.1.0]hexane-6-carboxylate,
n-octyl(1S,5R,6S)-2-oxobicyclo[3.1.0]hexane-6-carboxylate,
allyl(1S,5R,6S)-2-oxobicyclo[3.1.0]hexane-6-carboxylate,
benzyl(1S,5R,6S)-2-oxobicyclo[3.1.0]hexane-6-carboxylate,
4-chlorobenzyl(1S,5R,6S)-2-oxobicyclo[3.1.0]hexane-6-carboxylate,
4-methoxybenzyl(1S,5R,6S)-2-oxobicyclo[3.1.0]hexane-6-carboxylate,
4-nitrobenzyl(1S,5R,6S)-2-oxobicyclo[3.1.0]hexane-6-carboxylate, 4-methylbenzyl(1S,5R,6S)-2-oxobicyclo[3.1.0]hexane-6-carboxylate,
2,4-dimethoxybenzyl(1S,5R,6S)-2-oxobicyclo[3.1.0]hexane-6-carboxylate,
2,4,6-trimethylbenzyl(1S,5R,6S)-2-oxobicyclo[3.10]hexane-6-carboxylate,
(S)-phenylethyl(1S,5R,6S)-2-oxobicyclo[3.1.0]hexane-6-carboxylate,
(R)-phenylethyl(1S,5R,6S)-2-oxobicyclo[3.1.0]hexane-6-carboxylate,
β-phenylethyl(1S,5R,6S)-2-oxobicyclo[3.1.0]hexane-6-carboxylate,
phenylpropyl(1S,5R,6S)-2-oxobicyclo[3.1.0]hexane-6-carboxylate,
triphenylmethyl(1S,5R,6S)-2-oxobicyclo[3.1.0]hexane-6-carboxylate,
phenyl(1S,5R,6S)-2-oxobicyclo[3.1.0]hexane-6-carboxylate,
4-methylphenyl(1S,5R,6S)-2-oxobicyclo[3.1.0]hexane-6-carboxylate,
4chlorophenyl(1S,5R,6S)-2-oxobicyclo[3.1.0]hexane-6-carboxylate,
4-methoxyphenyl(1S,6R,6S)-2-oxobicyclo[3.1.0]hexane-6-carboxylate,
4-nitrophenyl(1S,5R,6S)-2-oxobicyclo[3.1.0]hexane-6-carboxylate,
2-naphthyl(1S,6R,6S)-2-oxobicyclo[3.1.0]hexane-6-carboxylate,
methyl(1R,5S,6R) -2-oxobicyclo[3.1.0]hexane-6-carboxylate,
ethyl(1R,5S,6R)-2-oxobicyclo[3.1.0]hexane-6-carboxylate,
n-propyl(1R,5S,6R)-2-oxobicyclo[3.1.0]hexane-6-carboxylate,
isopropyl (1R,5S,6R)-2-oxobicyclo[3.1.0]hexane-6-carboxylate,
n-butyl(1R,5S,6R)-2-oxobicyclo[3.1.0]hexane-6-carboxylate,
isobutyl(1R,5S,6R)-2-oxobicyclo[3.1.0]hexane-6-carboxylate,
sec-butyl(1R,5S,6R)-2-oxobicyclo[3.1.0]hexane-6-carboxylate,
t-butyl(1R,5S,6R)-2-oxobicyclo[3.1.0]hexane-6-carboxylate,
n-pentyl(1R,5S,6R)-2oxobicyclo[3.1.0]hexane-6-carboxylate,
isopentyl(1R,6S,6R)-2-oxobicyclo[3.1.0]hexane-6-carboxylate,
neopentyl(1R,5S,6R)-2-oxobicyclo[3.1.0]hexane-6-carboxylate,
n-hexyl(1R,5S,6R)-2-oxobicyclo[3.1.0]hexane-6-carboxylate,
cyclohexyl(1R,5S,6R)-2-oxobicyclo[3.1.0]hexane-6-carboxylate,
n-heptyl(1R,5S,6R)-2-oxobicyclo[3.1.0]hexane6-carboxylate,
cycloheptyl(1R,5S,6R)-2-oxobicyclo[3.1.0]hexane-6-carboxylate,
n-octyl(1R,5S,6R)-2-oxobicyclo[3.1.0]hexane-6-carboxylate,
allyl(1R,5S,6R)-2-oxobicyclo[3.1.0]hexane-6-carboxylate,
benzyl(1R,5S,6R)-2-oxobicyclo[3.1.0]hexane-6-carboxylate,
4-chlorobenzyl(1R,5S,6R)-2-oxobicyclo[3.1.0]hexane-6-carboxylate,
4-methoxybenzyl(1R,5S,6R)-2-oxobicyclo[3.1.0]hexane-6-carboxylate,
4-nitrobenzyl(1R,5S,6R)-2-oxobicyclo[3.1.0]hexane-6-carboxylate,
4-methylbenzyl(1R,5S,6R)-2-oxobicyclo[3.1.0]hexane-6-carboxylate, (2,4-dimethoxybenzyl) (1R,5S,6R)-2-oxobicyclo[3.1.0]hexane-6-carboxylate,
2,4,6-trimethylbenzyl(1R,5S,6R)-2-oxobicyclo[3.1.0]hexane-6-carboxylate,
(S)-phenylethyl(1R,5S,6R)-2-oxobicyclo[3.1.0]hexane-6-carboxylate,
(R)-phenylethyl(1R,5S,6R)-2-oxobicylo[3.1.0]hexane-6-carboxylate,
β-phenylethyl(1R,5S,6R)-2-oxobicyclo[3.1.0]hexane-6-carboxylate,
phenylpropyl(1R,6S,6R)-2-oxobicyclo[3.1.0]hexane-6-carboxylate,
benzhydryl, (1R,5S,6R)-2-oxobicyclo[3.1.0]hexane-6-carboxylate,
triphenylmethyl(1R,5S,6R)-2-oxobicyclo[3.1.0]hexane-6-carboxylate,
phenyl(1R,5S,6 R)-2-oxobicyclo[3.1.0]hexane-6-carboxylate,
4-methylphenyl(1R,5S,6R)-2-oxobicyclo[3.1.0]hexane-6-carboxylate,
4-chlorophenyl(1R,5S,6R)-2-oxobicyclo[3.1.0]hexane-6-carboxylate,
4-methoxyphenyl(1R,5S,6R)-2-oxobicyclo[3.1.0]hexane-6-carboxylate,
4-nitrophenyl( 1R,5S,6R)-2-oxobicyclo[3.1.0]hexane-6-carboxylate,
2-naphthyl(1R,5S,6R)-2-oxobicyclo[3.1.0]hexane-6-carboxylate.

In addition, compounds which are further substituted at the 3- and 4-positions independently in the above-described compounds with a group selected from a halogen atom, nitro group, methyl group, ethyl group, n-propyl group, isopropyl group, n-butyl group, isobutyl group, sec-butyl group, t-butyl group, n-pentyl group, isopentyl group, neopentyl group, n-hexyl group, n-heptyl group, n-octyl group, cyclohexyl group, cycloheptyl group;

allyl group, propynyl group, 2-naphthyl group, phenyl group, 2-fluorophenyl group, 3-fluorophenyl group, 4fluorophenyl group, 3,4-difluorophenyl group, pentafluorophenyl group, 2-chlorophenyl group, 3-chlorophenyl group, 4-chlorophenyl group, 3,4dichlorophenyl group, 2,5-dichlorophenyl group, 2-bromophenyl group, 3-bromophenyl group, 4-bromophenyl group, 2-methylphenyl group, 3-methylphenyl group, 4-methylphenyl group, 2-methoxyphenyl group, 3-methoxyphenyl group, 4-methoxyphenyl group, 4-nitrophenyl group, benzyl group, 2-fluorobenzyl group, 3-fluorobenzyl group, 4-fluorobenzyl group, 2,3-difluorobenzyl group, 2,4-difluorobenzyl group, 2,5-difluorobenzyl group, 3,5-difluorobenzyl group, 3,4-difluorobenzyl group, 2,3,4-trifluorobenzyl group, 2-chlorobenzyl group, 3-chlorobenzyl group, 4-chlorobenzyl group, 2,3-dichlorobenzyl group, 3-chloro-4-fluorobenzyl group, 2-methylbenzyl group, 3-methylbenzyl group, 4-methylbenzyl group, 4-fluoro-3-methylbenzyl group, 3-fluoro-2-methylbenzyl group, 3,5-dimethylbenzyl group, 4-isopropylbenzyl group, 2,4-dimethylbenzyl group, 2,5-dimethylbenzyl group, 2,4,6-trimethylbenzyl group, 2-methoxybenzyl group, 3-methoxybenzyl group, 4-methoxybenzyl group, 2,4-dimethoxybenzyl group, 3-fluoro-4-methoxybenzyl group, 3-methyl-4methoxybenzyl group, 4-phenylbenzyl group, 4-nitrobenzyl group, α-phenylethyl group, β-phenylethyl group, phenylpropyl group, benzhydryl group, triphenylmethyl group, 2-pyrimidyl group, azetidine-1-yl group, azetidine-2-yl group, pyrrolidine-2-yl group, piperidine-3-yl group, and an indanyl, 1,2,3,4-tetrahydronaphtho-1-yl, 2,3-dihydrobenzopyran-2-yl and xanthene-9-yl group.

According to the present invention, the optically active 2-oxobicyclo[3.1.0]hexane-6-carboxylic acids of formula (2a) or (2b) and the optically active 2-oxobicyclo[3.1.0] hexane-6-carboxylates of formula (3a) or (3b) can be resolved easily and efficiently by the present method.

EXAMPLES

Hereinafter, the present invention is described in more detail by reference to the Examples, which however are not be construed to limit the scope of the present invention thereto.

In the Examples, racemic ethyl(1SR,5RS,6SR)-2-oxobicyclo [3.1.0]hexane-6-carboxylate usually means a mixture containing an equal amount of ethyl(1S,5R,6S)-2-oxobicyclo[3.1.0]hexane-6-carboxylate and ethyl(1R,5S, 6R)-2-oxobicyclo[3.1.0]hexane-6-carboxylate.

Examples 1 to 8

As the present enzyme, each of the various commercial enzymes shown in Table 1 was added in an amount shown in Table 2 to 1 ml of 100 mM phosphate buffer (pH 7.0) and dissolved therein. 10 mg of racemic ethyl (1SR,5RS,6SR)-2-oxobicyclo[3.1.0]hexane-6-carboxylate was dissolved in 1 ml n-hexane, then added to the enzyme solution, and heated to 40° C. and the mixture was stirred. After the time shown as the reaction time in Table 2 elapsed, an aliquot of the reaction solution was removed and analyzed by HPLC [column: Sumichiral OA-5000, 4.6 mmφ×15 cm (Shumika Bunseki Center)], and the optical purity and reaction yield of the formed 2-oxobicyclo [3.1.0]hexane-6-carboxylic acid were determined. (−)-(1R,5S,6R)-2-oxobicyclo [3.1.0] hexane6-carboxylic acid was obtained in excess. The results are shown in Table 2.

Examples 9 to 36

Each of the various commercial enzymes shown in Table 3 was added in an amount shown in Table 4 to 1 ml of 100 mM phosphate buffer (pH 7.0) and dissolved therein. 10 mg of racemic ethyl(1SR,5RS,6SR)-2-oxobicyclo [3.1.0] hexane-6-carboxylate was dissolved in 1 ml n-hexane, then added to the enzyme solution, and heated to 40° C. and the mixture was stirred. After the time shown as the reaction time in Table 4 elapsed, an aliquot of the reaction solution was removed and analyzed in the same manner as in Examples 1 to 8 to determine the optical purity and reaction yield of the formed 2-oxobicyclo[3.1.0]hexane-6-carboxylic acid. (+)-(1S,5R, 6S)-2-oxobicyclo[3.1.0]hexane-6-carboxylic acid was obtained in excess. The results are shown in Table 4.

TABLE 1

| Examples | Enzyme name | Origin of the enzyme | Enzyme maker |
| --- | --- | --- | --- |
| 1 | CHIRAZYME E-4 | thermophilic micro-organism | Roche Diagnostics |
| 2 | Lipase OF360 | *Candida cylindracea* | Meito Sangyo K.K. |
| 3 | Esterase 46054 | *Bacillus thermoglucosidasius* | Fluka |
| 4 | CHIRAZYME E-3 | thermophilic micro-organism | Roche Diagnostics |
| 5 | Cholesterol Esterase | *Candida rugosa* | Roche Diagnostics |
| 6 | α-Chymotrypsin | Bovine Pancreas | SIGMA |
| 7 | γ-Chymotrypsin | Bovine Pancreas | SIGMA |
| 8 | δ-Chymotrypsin | Bovine Pancreas | SIGMA |

TABLE 2

| Examples | Amount of the enzyme (mg) | Reaction time (hr) | Reaction yield (%) | Optical purity (% ee) | Optical isomer in excess |
| --- | --- | --- | --- | --- | --- |
| 1 | 2.0 | 24 | 29.0 | 72.9 | (−)-isomer |
| 2 | 2.0 | 24 | 18.5 | 68.5 | (−)-isomer |
| 3 | 2.0 | 2 | 26.9 | 65.1 | (−)-isomer |
| 4 | 2.0 | 4 | 30.4 | 58.6 | (−)-isomer |
| 5 | 2.0 | 24 | 6.7 | 58.8 | (−)-isomer |
| 6 | 2.1 | 24 | 4.8 | 40.5 | (−)-isomer |
| 7 | 2.1 | 24 | 4.6 | 32.0 | (−)-isomer |
| 8 | 10.1 | 24 | 9.4 | 129.1 | (−)-isomer |

TABLE 3

| Examples | Enzyme name | Origin of the enzyme | Enzyme maker |
| --- | --- | --- | --- |
| 9 | CHIRAZYME L-5 | *Candida antarctica* | Roche Diagnostics |
| 10 | CHIRAZYME L-6 | Pseudomonas sp. | Roche Diagnostics |
| 11 | Cholesterol Esterase | Pseudomonas sp. | Wako Pure Chemical Industries, Ltd. |
| 12 | CHIRAZYME L-2 | *Candida antarctica* | Roche Diagnostics |
| 13 | Toyozyme | *Pseudomonas aeruginosa* | Toyobo Co., Ltd. |
| 14 | Lipase 62285 | *Aspergillus oryzae* | Fluka |
| 15 | LIPOSAM | Pseudomonas sp. | Showa Denko, K.K |
| 16 | Lipase (immobilized product) | Pseudomonas sp. | Wako Pure Chemical Industries, Ltd. |
| 17 | CHIRAZYME L-8 | Humicola sp. | Roche Diagnostics |

TABLE 3-continued

| Examples | Enzyme name | Origin of the enzyme | Enzyme maker |
|---|---|---|---|
| 18 | CHIRAZYME E-5 | thermophilic micro-organism | Roche Diagnostics |
| 19 | Lipase AL | Achromobacter sp. | Meito Sangyo K.K |
| 20 | Kitopearl Cholesterol Esterase CEN | Pseudomonas sp. | Fuji Spinning Co., Ltd. |
| 21 | Kitopearl Lipase-AP | Bacteria | Fuji Spinning Co., Ltd. |
| 22 | Kitopearl Lipase-CV | *Cromobacterium viscosum* | Fuji Spinning Co., Ltd |
| 23 | Lipase | *Cromobacterium viscosum* | Asahi Chemical Industry Co., Ltd. |
| 24 | Lipase QL | Alcaligenes sp. | Meito Sangyo K.K. |
| 25 | Lipase AH | *Pseudomonas cepacia* | Amano Pharmaceutical Co., Ltd. |
| 26 | Lipase AK 20 | *Pseudomonas fluorescens* | Amano Pharmaceutical Co., Ltd. |
| 27 | Lipase | *Mucor miehei* | Biocatalysts Ltd. |
| 28 | Protease P 3 | *Aspergillus melleus* | Amano Pharmaceutical Co., Ltd. |
| 29 | Lipase 62291 | *Rhizoinucor miehei* | Fluka |
| 30 | CHIRAZYME P-1 | *B. licheniformis* | Roche Diagnostics |
| 31 | Prolazer | Bacillus sp. | Amano Pharmaceutical Co., Ltd. |
| 32 | Acylase I | Pig kidney | Wako Pure Chemical Industries, Ltd. |
| 33 | Lipase PL | Alcaligenes sp. | Meito Sangyo K.K. |
| 34 | CHIRAZYME L-9 | *Mucor miehei* | Roche Diagnostics |
| 35 | Protease N | *Bacillus subtilis* | Amano Pharmaceutical Co., Ltd. |
| 36 | CHIRAZYME L-10 | Alcaligines sp | Roche Diagnostics |

TABLE 4

| Examples | Amount of the enzyme (mg) | Reaction time (hr) | Reaction yield (%) | Optical purity (% ee) | Optical isomer in excess |
|---|---|---|---|---|---|
| 9 | 2.0 | 24 | 23.2 | 98.0 | (+)-isomer |
| 10 | 0.1 | 4 | 7.3 | 82.9 | (+)-isomer |
| 11 | 0.1 | 4 | 10.1 | 78.2 | (+)-isomer |
| 12 | 0.1 | 4 | 55.0 | 59.7 | (+)-isomer |
| 13 | 5.1 | 24 | 17.9 | 75.0 | (+)-isomer |
| 14 | 10 | 24 | 10.7 | 75.4 | (+)-isomer |
| 15 | 0.1 | 4 | 7.5 | 74.9 | (+)-isomer |
| 16 | 10.2 | 24 | 42.2 | 64.8 | (+)-isomer |
| 17 | 2.1 | 24 | 13.3 | 72.3 | (+)-isomer |
| 18 | 10 | 24 | 20.2 | 62.1 | (+)-isomer |
| 19 | 5.2 | 24 | 14.9 | 56.0 | (+)-isomer |
| 20 | 2.0 | 24 | 11.9 | 52.1 | (+)-isomer |
| 21 | 2.0 | 24 | 5.6 | 51.7 | (+)-isomer |
| 22 | 2.1 | 24 | 5.0 | 49.7 | (+)-isomer |
| 23 | 2.1 | 24 | 46.5 | 37.9 | (+)-isomer |
| 24 | 2.0 | 24 | 3.6 | 49.3 | (+)-isomer |
| 25 | 10.1 | 24 | 45.2 | 34.6 | (+)-isomer |
| 26 | 10.2 | 24 | 14.0 | 37.1 | (+) isomer |
| 27 | 2.2 | 24 | 55.8 | 26.1 | (+)-isomer |
| 28 | 2.1 | 24 | 5.9 | 37.2 | (+)-isomer |
| 29 | 2.6 | 24 | 38.2 | 29.7 | (+)-isomer |
| 30 | 2.3 | 24 | 54.0 | 24.9 | (+)-isomer |
| 31 | 2.5 | 24 | 11.1 | 34.3 | (+)-isomer |
| 32 | 0.1 | 4 | 60.8 | 20.6 | (+)-isomer |
| 33 | 2.0 | 24 | 7.0 | 27.5 | (+)-isomer |
| 34 | 1.0 | 4 | 5.4 | 24.1 | (+)-isomer |
| 35 | 2.3 | 24 | 7.8 | 18.2 | (+)-isomer |
| 36 | 2.0 | 24 | 4.8 | 17.3 | (+)-isomer |

Reference Example 1

A recombinant micro organism transformed by introducing a gene of the present enzyme derived from Chromobacterium SC-YM-1 was prepared according to a method described in JP-A 7-213280. That is, plasmids carrying an esterase gene derived from Chromobacterium SC-YM-1 (FERM BP-6703 transferred from FERM P-14009) and subjected to site-directed mutagenesis, that is, plasmids pCCA363term, pCCN43SA363term, pCC160S189Y363term and pCC160S 189F363term, were constructed and introduced respectively into *E. coli* JM 109 whereby recombinant microorganisms were prepared.

Hereinafter, the method of preparing these recombinant microorganisms is described.

1. Construction of Mutation Primers

As mutation primers for amino acid substitution i.e. Asn43Ser, Gly160Ser, Gly189Tyr, Gly189Phe, or Ala363 Term (termination codon), oligonucleotides having a nucleotide sequence corresponding to each amino acid (mutation primers: N43S (SEQ ID NO:1), I60S (SEQ ID NO:2), 189Y (SEQ ID NO:3), 189F (SEQ ID NO:4), A363 Term (SEQ ID NO:5), RV-G (SEQ ID NO:6), RV-C (SEQ ID NO:7), RV-D (SEQ ID NO:8), MY-3 (SEQ ID NO:9), MY-1 (SEQ ID NO:10) and MY-2 (SEQ ID NO:11) were synthesized. These mutation primers were synthesized in a DNA synthesizer, model 394 (Applied Biosystems) and then purified with an oligonucleotide purification cartridge (Applied Biosystems).

2. Site-directed Mutagenesis

A mutant esterase was prepared according to the method of Olfert Landt et al. (Gene, 96, 125–128, 1990).

2-1) Construction of plasmid pCCN43S

Plasmid pCC101 (FIG. 1) containing a wild-type esterase gene derived from Chromobacterium SC-YM-1 was constructed according to a method described in Examples 1 to 5 in JP-A 7-213280. PCR was conducted using 500 ng of the resulting pCC101 as template DNA, mutation primer RV-G (SEQ ID NO:6) (100 pmol), mutation primer N43S (SEQ ID NO:1) (100 pmol) and GeneAmpTM PCR Reagent Kit (Takara Shuzo Co., Ltd.) thereby amplifying the DNA fragment. The resulting PCR product (190 bp fragment) was purified by use of a SUPREC-02 (Takara Shuzo Co., Ltd.) column.

Then, PCR was conducted in a similar manner using 500 ng of pCC101 as template DNA, mutation primer MY-3 (SEQ ID NO:9) (50 pmol) and the previously prepared 190 bp DNA fragment (50 pmol) as primer and GeneAmpTM PCR Reagent Kit thereby amplifying the DNA fragment. The amplified DNA fragment was digested with restriction enzymes NdeI and Bpu1102I, and the sample was electrophoresed in 4% agarose gel (NuSieve 3:1 Agarose (Takara Shuzo Co., Ltd.)), and about 370 bp DNA fragment was recovered and purified by use of a Gene Clean DNA purification kit (BIO101).

Figure 2:
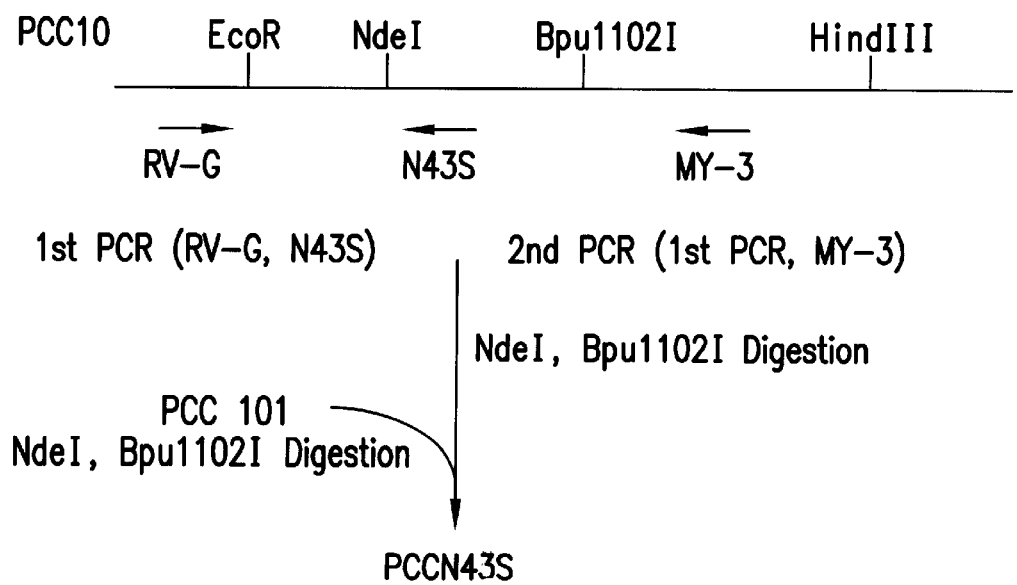
FIG. 2 shows the process of constructing recombinant plasmid pCCN43S.

Separately, 3 µg of pCC101 was digested with NdeI and Bpu1102I and treated with alkaline phosphatase. Then, the resulting NdeI-Bpu1102I fragment (4.2 kbp) from PCC101 was ligated by use of a DNA ligation kit (Takara Shuzo Co., Ltd.) to the mutated NdeI-Bpu11021 fragment (240 bp) previously prepared, and the resulting construct was introduced into E. coli JM109 to prepare pCCN43S (FIG. 2).

2-2) Construction of Plasmid pCC160S

PCR was conducted using plasmid pCC101 (0.5 µg) as template DNA, mutation primer MY-1 (SEQ ID NO:10) (100 pmol), mutation primer 160S (SEQ ID NO:2) (100 pmol) and GeneAmp PCR Reagent Kit (Takara Shuzo Co., Ltd.), thus amplifying the DNA fragment. The resulting PCR product (270 bp DNA fragment) was purified by use of a SUPREC-02 (Takara Shuzo Co., Ltd.) column.

Then, PCR was conducted similarly using pCC101 (0.5 µg) as template DNA, mutation primer RV-C (SEQ ID NO:7) (50 pmol) and the previously prepared 270 bp DNA fragment (50 pmol) as primer and GeneAmp PCR Reagent Kit, thus amplifying the DNA fragment. The amplified DNA fragment was digested with restriction enzymes CelIII and ClaI, and the sample was electrophoresed in 4% agarose gel (NuSieve 3:1 Agarose (Takara Shuzo Co., Ltd.)), and about 240 bp DNA fragment was recovered and purified by use of a Gene Clean DNA purification kit BIO101).

Separately, pCC101 (3 µg) was digested with CelIII and ClaI and treated with alkaline phosphatase. Then, the resulting DNA fragment (4.2 kbp) was ligated by use of a DNA ligation kit (Takara Shuzo Co., Ltd.) to the about 240 bp mutated DNA fragment previously prepared, and the resulting construct was introduced into E. coli JM109 to prepare pCC160S.

2-3) Construction of Plasmid pCC189Y

Plasmid pCC189Y was constructed in the same manner as in construction of plasmid pCC160S except that mutation primer 189Y (SEQ ID NO:3) was used in place of mutation primer 160S used in construction of pCC160S.

2-4) Construction of Plasmid pCC 189F

Plasmid pCC189F was constructed in the same manner as in construction of plasmid pCC160S except that mutation primer 189F (SEQ ID NO:4) was used in place of mutation primer 160S used in construction of pCC160S.

2-5) Construction of pCCA363term

PCR was conducted using 600 ng of pCC101 as template DNA, mutation primer MY-2 (SEQ ID:11) (100 pmol), mutation primer A363term (SEQ ID NO:5) (100 pmol) and GeneAmpTM PCR Reagent Kit (Takara Shuzo Co., Ltd.) to amplify the DNA fragment. The resulting PCR product (150 bp fragment) was purified by a SUPREC-02 (Takara Shuzo Co., Ltd.) column.

Then, PCR was conducted using 500 ng of pCC101 as template DNA, mutation primer RV-D (SEQ ID:5) (50 pmol), the previously purified 150 bp DNA fragment (50 mol) as a primer and GeneAmpTM PCR Reagent Kit (Takara Shuzo Co., Ltd.) to amplify the DNA fragment. The amplified DNA fragment was digested with restriction enzymes BstPI and XbaI and then electrophoresed in 4% agarose gel (NuSieve 3:1 Agarose (Takara Shuzo Co., Ltd.)) to separate an about 220 bp DNA fragment which was then purified by a Gene Clean DNA purification kit.

Figure 3:
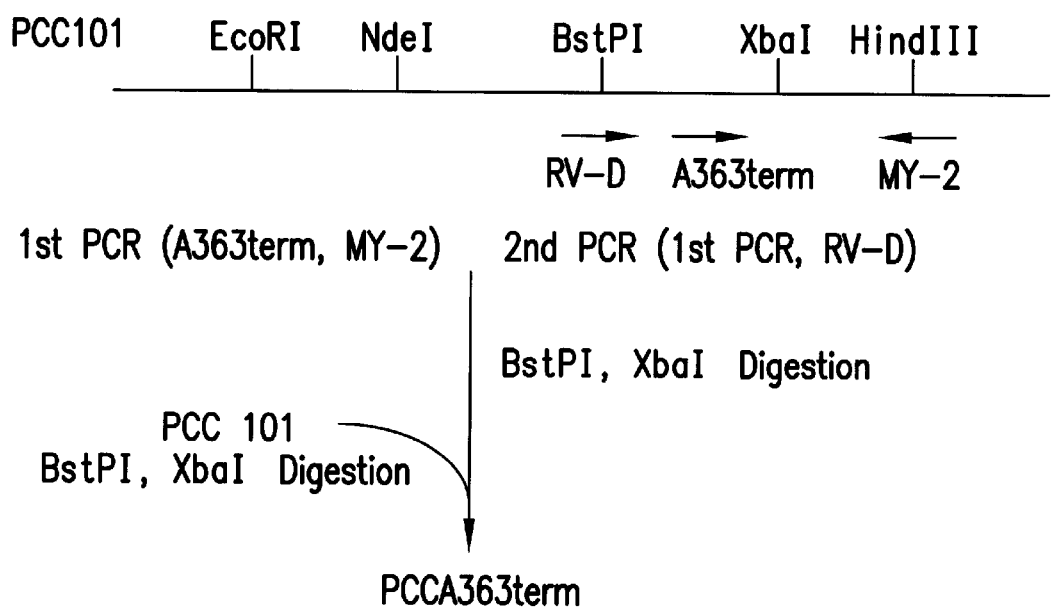
FIG. 3 shows the process of constructing recombinant plasmid pCCA363term.

Separately, 3 µg of pCC101 was digested with BstPI and XbaI and treated with alkaline phosphatase. Then, the resulting BstPI-XbaI fragment (4.2 kbp) from pCC101 was ligated to the previously constructed mutated BstPI-XbaI fragment (220 bp) by use of a DNA ligation kit (Takara Shuzo Co., Ltd.) and then introduced in a usual manner into E. coli JM 109 to construct pCCA363term (FIG. 3).

3. Multiple Mutation

3-1) Construction of pCCN43SA363term

Figure 4:
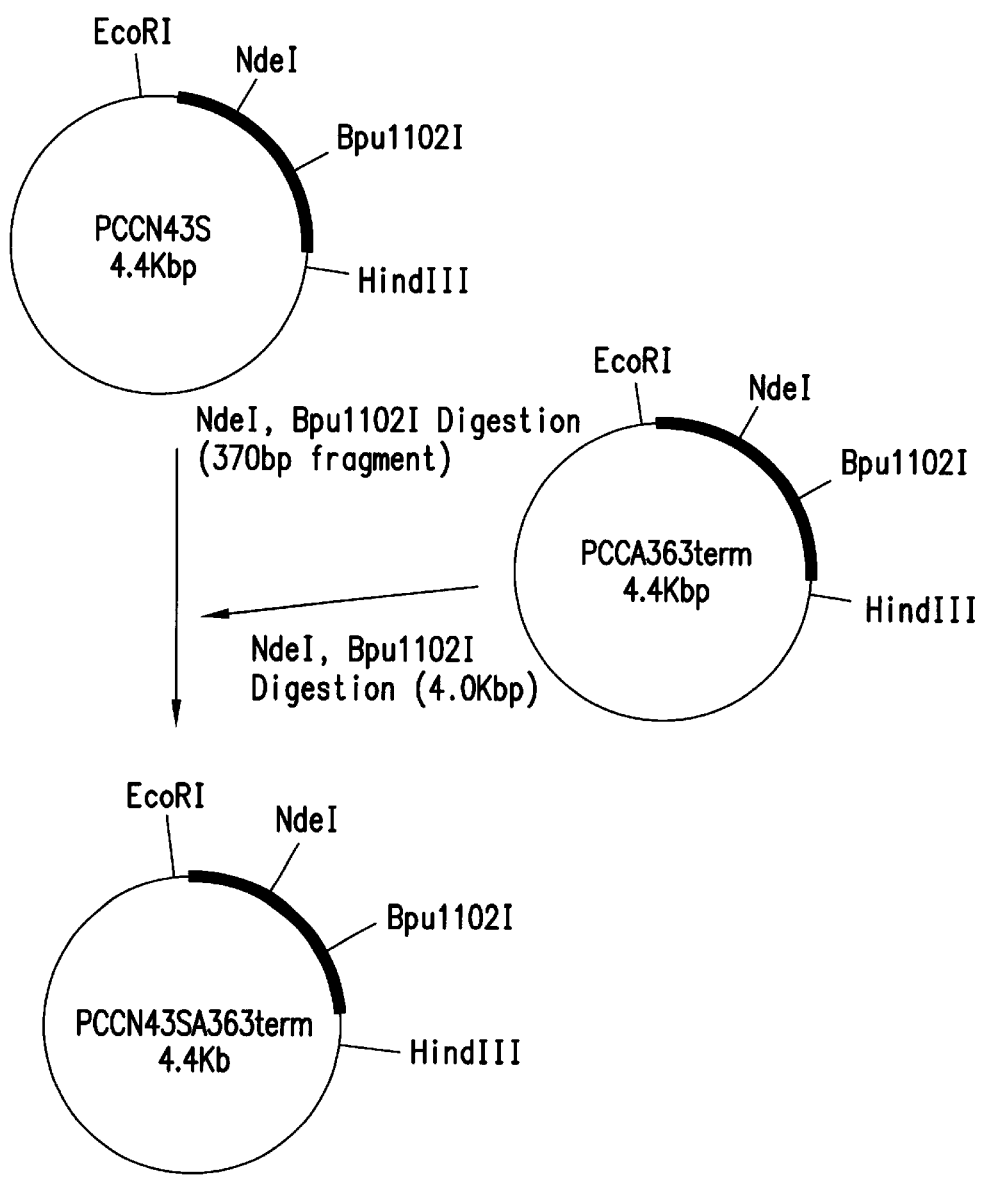
FIG. 4 shows the process of constructing recombinant plasmid pCCN43SA363term.

10 µg of pCCN43S obtained in 2-1) was digested with NdeI and Bpu1102I to give a 370 bp fragment. Separately, 3 µg of pCCA363term obtained in 2-5) was digested with NdeI and Bpu1102I and treated with alkaline phosphatase. Then, the resulting NdeI-Bpu11021 fragment (4.2 kbp) from pCCA368term was ligated to the previously prepared NdeI-Bpu1102I fragment (370 bp) by use of a DNA ligation kit (Takara Shuzo Co., Ltd.) and then introduced into E. coli JM 109 whereby plasmid pCCN43SA363term containing a multiple-mutant esterase gene was obtained (FIG. 4).

3-2) Construction of Plasmid pCC160S189YA363term

Three kinds of DNA fragments, that is, 0.6 kbp DNA fragment obtained by digesting the mutant plasmid pCC160S (10 µg) obtained in 2-2) with restriction enzymes EcoRI and FspI, 0.4 kbp fragment obtained by digesting the mutant plasmid pCC189Y (10 µg) obtained in 2-3) with FspI and BstPI, and 3.4 kbp DNA fragment obtained by digesting plasmid pCCA363term (3 µg) with restriction enzymes BstPI and EcoRI , were ligated to one another by use of a DNA ligation kit (Takara Shuzo Co., Ltd.) and then introduced into E. coli JM 109, whereby plasmid pCC160S189YA363term containing a multiple-mutant esterase gene was obtained.

3-3) Construction of Plasmid pCC160S189FA363term

Three kinds of DNA fragments, that is, 0.6 kbp DNA fragment obtained by digesting the mutant plasmid pCC160S (10 µg) obtained in 2-2) with restriction enzymes EcoRI and FspI, 0.4 kbp fragment obtained by digesting the mutant plasmid pCC189F (10 µg) obtained in 2-4) with FspI and BstPI, and 3.4 kbp DNA fragment obtained by digesting plasmid pCCA363term (3 µg) obtained in 2-5) with restriction enzymes BstPI and EcoRI, were ligated to one another by use of a DNA ligation kit (Takara Shuzo Co., Ltd.) and then introduced into E. coli JM 109, whereby plasmid pCC160S189FA363term containing a multiple-mutant esterase gene was obtained.

4. Preparation of Transformants

Plasmids pCCN43SA363term, pCC160S189YA363term, pCC160S189FA363term and pCCA363term were introduced into E. coli JM 109 respectively to prepare recombinant microorganisms JM109/pCCN43SA363term, JM109/ pCC160S189YA363term, JM109/pCC160S189FA363term and JM109/pCCA863term, respectively.

Reference Example 2

100 ml liquid medium (prepared by dissolving 5 g glycerol, 6 g yeast extract and 9 g monopotassium phosphate and 4 g dipotassium phosphate in 1 L water and adjusting it to pH 7.0) was introduced into a 500 ml Erlenmeyer flask and sterilized, and ampicillin was added thereto at a concentration of 50 μg/ml. The recombinant microorganism JM109/pCCN43SA363term prepared in Reference Example 1 was inoculated from a slant culture via one loop of platinum into the medium and cultured at 30° C. for 24 hours under shaking. Then, 1500 ml liquid medium (prepared by dissolving 15 g glycerol, 25 g yeast extract, 0.4 g monopotassium phosphate, 2 g magnesium sulfate and 0.1 g ferrous sulfate in 1 L water and adjusting it to pH 7.0) was sterilized and introduced into a 3-L small culture chamber (MDL model, Mitsubishi Bioenzi Co., Ltd.). Then, 15 ml of the above culture liquid in the Erlenmeyer flask was inoculated into it. The microorganism was cultured at 30° C. with stirring under aeration, and IPTG (isopropylthio-β-D-galactoside) was added thereto at a final concentration of 1 mM at a middle stage in the logarithmic growth phase (10 to 15 hours of culture). After an additional sterilized medium was added thereto, the microorganism was cultured for 40 hours in total whereby a culture of the microorganism was obtained.

Reference Examples 3 to 6

A microbial culture of each of the genetically recombinant microorganisms JM109/pCC160A189YA363term, JM109/pCC160S189YA363term, JM109/pCC160S189FA363term and JM109/pCCA363term was obtained in the same manner as in Reference Example 2

Reference Example 7

A microbial culture obtained from the recombinant microorganism JM109/pCCN43SA363term in the same manner as in Reference Example 2 was centrifuged (12000×g, 30 minutes, 4° C.) to give the wet microorganism. This wet microorganism was sonicated (20 KHz, 15 minutes, 4° C.) and centrifuged (12000×g, 30 minutes, 4° C.) to give its supernatant. 150 ml of the resulting supernatant was passed through a column charged with 200 ml anion-exchange column (DEAE-Sepharose fast flow, Pharmacia). After the column was washed with 0.15 M NaCl+10 mM Tris-HCl buffer (pH 7.5), the desired enzyme was eluted with a linear gradient of from 0.15 to 0.35 M NaCl. The activity of the eluted fractions was measured using p-nitrophenyl acetate (pNPA) which is a general substrate for esterase. Specifically, the substrate dissolved in acetonitrile was added to give a final concentration of 5 mM to 1.0 ml of 10 mM phosphate buffer (pH 7.5) containing the eluted fraction and then kept at 37° C., the increase in absorbance at 410 nm was measured. Fractions with the esterase activity were collected and passed through a column charged with 200 ml hydrophobic resin (Butyl-Toyopearl 650S, Tosoh Corporation). After the colon was washed with 10% (W/V) $(NH_4)_2SO_4$+10 mM Tris-HCl buffer (pH 7.5), the. desired enzyme was eluted with a linear gradient of from 10 to 0% (W/V) saturated ammonium sulfate. Fractions with the esterase activity were collected to give a purified enzyme (hereinafter, this purified enzyme is referred to as N43SA363term.).

Reference Examples 8 to 11

From cultures of the recombinant microorganisms JM109/pCC160A189YA363term, JM109/pCC160S189YA363term, JM109/pCC160S189FA363term and JM109/pCCA363term, their purified enzymes were obtained respectively in the same manner as in Reference Example 7 (hereinafter, these purified enzymes are referred to as 160A189YA363term, 160S189YA363term, 160S189FA363term and A363term, respectively.).

Reference Example 12

A recombinant microorganism transformed with a gene of the present enzyme derived from Arthrobacter SC-6-98-28 was prepared according to a method described in JP-A 5-56787.

That is, plasmid pAGE-1 containing an esterase gene derived from Arthrobacter SC-6-98-28 was prepared according to a method described in the Examples in JP-A 5-56787. A region coding for esterase was cleaved off by digestion with restriction enzymes NspV and HindIII and then ligated to a DNA fragment synthesized for converting the initiation codon GTG in the esterase gene into ATG and then to expression vector $pUC_{118}$ (Takara Shuzo Co., Ltd.) digested with restriction enzymes BamHI and HindIII. An expression vector for *E. coli* comprising the esterase gene derived from Arthrobacter SC-6-98-28 located downstream from a lac promoter in pUC118 was thus constructed, and this plasmid was transformed into *E. coli* JM 105 to prepare a recombinant microorganism.

Reference Example 13

100 ml liquid medium (prepared by dissolving 5 g glycerol, 6 g yeast extract, 9 g monopotassium phosphate and 4 g dipotassium phosphate in 1 L water and adjusting it to pH 7.0) was introduced into a 500 ml Erlenmeyer flask and sterilized, and ampicillin was added thereto at a concentration of 50 μg/ml. The recombinant microorganism prepared in Reference Example 12 was inoculated from a slant culture via one loop of platinum into the medium and cultured at 30° C. for 24 hours under shaking. Then, 1500 ml liquid medium (prepared by dissolving 15 g glycerol, 25 g yeast extract, 0.4 g monopotassium phosphate, 2 g magnesium sulfate and 0.1 g ferrous sulfate in 1 L water and adjusting it to pH 7.0) was sterilized and introduced into a 3-L small culture chamber (MDL model, Mitsubishi Bioenzi Co., Ltd.). Then, 15 ml of the above culture liquid in the Erlenmeyer flask was inoculated into it. The microorganism was cultured at 30° C. with stirring under aeration, and IPTG (isopropylthio-β-D-galactoside) was added thereto at a final concentration of 1 mM at a middle stage in the logarithmic growth phase (10 to 15 hours of culture). After an additional sterilized medium was added thereto, the microorganism was cultured for 40 hours in total whereby a culture of the microorganism was obtained.

Reference Example 14

The recombinant microorganism JM109/pAL612 (FERM-BP 5740) transformed by introducing a gene of the present enzyme derived from Burkholderia cepacia SC-20 was cultured at 37° C. for 16 hours in 100 ml LB medium (Difco) containing 50 mg/L ampicillin and 1 mM IPTG (isopropylthio-β-D-galactoside) and recovered by centrifugation (6000 rpm, 10 minutes). The recovered microorganism was suspended in 10 ml of 100 mM phosphate buffer (H 7.0), sonicated (10 minutes) and centrifuged whereby a crude enzyme extract was obtained. The resulting crude enzyme extract was lyophilized whereby a crude enzyme powder was obtained.

Examples 37 to 41

Each of the purified enzymes obtained in Reference Examples 7 to 11 was added to, and suspended in, 1 ml of 100 mM phosphate buffer (pH 7.0). 10 mg of racemic ethyl(1SR,5RS,6SR)-2-oxobicyclo[3.1.0]hexane-6-carboxylate was dissolved in 1 ml n-hexane, then added to each enzyme solution, and heated to 40° C., and the mixture was stirred. After the time shown as the reaction time in Table 5 elapsed, an aliquot of the reaction solution was removed and analyzed in the same manner as in Examples 1 to 8, and the formed 2-oxobicyclo[3.1.0]hexane-6-carboxylic acid was measured for its optical purity and reaction yield. The results are shown in Table 5.

TABLE 5

| Examples | The present enzyme | Amount of purified enzyme culture (μl) | Reaction time (hr) | Reaction yield (%) | Optical purity (% ee) | Optical isomer in excess |
| --- | --- | --- | --- | --- | --- | --- |
| 37 | 160A189YA363term | 10 | 2 | 34.3 | 80.5 | (−)-isomer |
| 38 | N43SA363term | 40 | 2 | 33.5 | 92.8 | (−)-isomer |
| 39 | 160S189YA363term | 10 | 6 | 36.7 | 86.5 | (−)-isomer |
| 40 | 160S189FA3G3term | 10 | 2 | 31.4 | 85.0 | (−)-isomer |
| 41 | A363term | 10 | 6 | 24.6 | 81.0 | (−)-isomer |

Example 42

2.0 mg of the culture obtained in Reference Example 13 from the transformant microorganism transformed with the gene of the present enzyme derived from Arthrobacter SC-6-98-28 was added to and suspended in 1 ml of 100 mM phosphate buffer (pH 7.0). 10 mg of racemic ethyl(1SR, 5RS,6SR)-2-oxobicyclo[3.1.0]hexane-6-carboxylate was dissolved in 1 ml n-hexane, added to the culture suspension, and heated to 40° C., and the mixture was stirred. After 13 hours, an aliquot of the reaction solution was removed and analyzed in the same manner as in Examples 1 to 8, and the formed 2-oxobicyclo[3.1.0]hexane-6-carboxylic acid was measured for optical purity and reaction yield. As a result, (+)-(1R,5S,6R)-2-oxobicyclo[3.1.0]hexane-6-carboxylic acid was obtained with 65.0% optical purity in 33.4% yield Example 43

2.0 mg of the crude enzyme powder of the present enzyme obtained in Reference Example 14 from Burkholderia cepacia SC-20 was added to, and suspended in, 1 ml of 100 mM phosphate buffer (pH 7.0). 10 mg of racemic ethyl(1SR, 5RS,6SR)-2-oxobicyclo[3.1.0]hexane-6-carboxylate was dissolved in 1 ml n-hexane, added to the enzyme solution, and heated to 40° C., and the mixture was stirred. After 13 hours, an aliquot of the reaction solution was removed and analyzed in the same manner as in Examples 1 to 8, and the formed 2-oxobicyclo[3.1.0]hexane-6-carboxylic acid was measured for optical purity and reaction yield. As a result, (+)-(1R,5S,6R)-2-oxobicyclo[3.1.0]hexane-6-carboxylic acid was obtained with 62.9% optical purity in 14.8% yield.

Example 44

10 μl of the purified enzyme 160A189YA363term obtained in Reference Example 8 from Chromobacterium SC-YM-1 was added to and suspended in 1 ml of 100 mM phosphate buffer (pH 7.0). 10 mg of racemic ethyl(1SR, 5RS,6SR)-2-oxobicyclo[3.10]hexane-6-carboxylate was dissolved in 1 ml n-hexane, added to the enzyme solution, and heated to 40° C., and the mixture was stirred. After 8 hours, the reaction solution was partitioned, and the aqueous layer was analyzed in the same manner as in Examples 1 to 8 to determine the optical purity and reaction yield of the formed 2-oxobicyclo[3.1.0]hexane-6-carboxylic acid. Further, the organic layer was analyzed by GC [column: CP-Cyclodextrin β-2,3,6-M-19, 0.25 mmφ×50 m, 0.25 μm (Chrompack Ltd.)] to determine the optical purity and reaction yield of the remaining unreacted ethyl 2-oxobicyclo [3.1.0]hexane-6-carboxylate. As a result, (−)-(1S,5R,6S)-2-oxobicyclo[2.1.0]hexane-6-carboxylic acid was obtained with 67.2% optical purity in 55.1% yield, and ethyl(+)-(1S, 5R, 6S)-2-oxobicyclo[3.1.0]hexane-6-carboxylate was obtained with 82.3% optical purity in 44.9% yield.

Example 45

40 μl of the purified enzyme N43SA363term obtained in Reference Example 7 from Chromobacterium SC-YM-1 was added to and suspended in 1 ml of 100 mM phosphate buffer (pH 7.0). 10 mg of racemic ethyl(1SR, 5RS,6SR)-2-oxobicyclo[3.1.0]hexane-6-carboxylate was dissolved in 1 ml n-hexane, added to the enzyme solution, and heated to 40° C., and the mixture was stirred. After 8 hours, the reaction solution was partitioned, and the formed 2-oxobicyclo[3.1.0]hexane-6-carboxylic acid and the remaining unreacted ethyl 2-oxobicyclo[3.1.0]hexane-6-carboxylate were measured respectively for optical purity and reaction yield in the same manner as in Example 44. As a result, (−)-(1R,5S,6R)-2-oxobicyclo[3.1.0]hexane-6-carboxylic acid was obtained with 68.7% optical purity in 58.7% yield, and ethyl(+)-(1S,5R,6S)-2-oxobicyclo[3.1.0] hexane-6-carboxylate was obtained with 97.6% optical purity in 41.3% yield.

Example 46

6.0 g of the culture obtained in Reference Example 3 from the transformant microorganism JM109/ pCC$_{160}$A189YA363term transformed with the gene of the present enzyme derived from Chromobacterium SC-YM-1 was added to and suspended in 400 ml of 100 mM phosphate buffer (pH 7.0). 40.0 g of racemic ethyl(1SR,5RS,6SR)-2-oxobicyclo[3.1.0]hexane-6-carboxylate was dissolved in 400 ml n-hexane, added to the enzyme solution, and heated to 40° C., and the mixture was stirred at 40° C. for 4 hours during which it was kept in the range of pH 7 to pH 8 by suitably adding 10% NaOH. Twelve N aqueous HCl was added to the reaction solution to adjust it to pH 4.2. Then, the reaction solution was filtered through Celite, ten adjusted to pH 7.6 with saturated aqueous NaHCO$_3$, and extracted and partitioned 4 times with 400 ml toluene, and the remaining unreacted ethyl 2-oxobicyclo[3.1.0]hexane-6-carboxylate was obtained from the organic layer. As a result of determination of optical purity and yield in the same manner as in Example 44, ethyl(+)-(1S,5R, 6S)-2-oxobicyclo[3.1.0] hexane-6-carboxylate was obtained with 100% optical purity in 26.5% yield.

Sequence Listing Free Text

SEQ ID NO:1 shows an oligonucleotide primer designed to introduce site-specific mutation Asn43Ser into the wild-type esterase derived from Chromobacterium SC-YM-1.

SEQ ID NO:2 shows an oligonucleotide primer designed to introduce site-specific mutation Gly160Ser into the wild-type esterase derived from Chromobacterium SC-YM-1.

SEQ ID NO:3 shows an oligonucleotide primer designed to introduce site-specific mutation Gly189Tyr into the wild-type esterase derived from Chromobacterium SC-YM-1.

SEQ ID NO:4 shows an oligonucleotide primer designed to introduce site-specific mutation Gly189Phe into the wild-type esterase derived from Chromobacterium SC-YM-1.

SEQ ID NO:5 shows an oligonucleotide primer designed to convert Ala363 into a termination codon in the wild-type esterase derived from Chromobacterium SC-YM-1.

SEQ ID NO:6 shows an oligonucleotide primer designed to introduce site-specific mutation Asn43Ser into the wild-type esterase derived from Chromobacterium SC-YM-1.

SEQ ID NO:7 shows an oligonucleotide primer designed to introduce site-specific mutation Gly160Ser, Gly189Tyr or Gly189Phe into the wild-type esterase derived from Chromobacterium SC-Ym-1.

SEQ ID NO;8 shows an oligonucleotide primer designed to convert Ala363 into a termination codon in the wild-type esterase derived from Chromobacterium SC-YM-1.

SEQ ID NO:9 shows an oligonucleotide primer designed to introduce site-specific mutation Asn43Ser into the wild-type esterase derived from Chromobacterium SC-YM-1.

SEQ ID NO:10 shows an oligonucleotide primer designed to introduce site-specific mutation Gly160Ser, Gly189Tyr or Gly189Phe into the wild type esterase derived from Chromobacterium SC-YM-1.

SEQ ID NO:11 shows an oligonucleotide primer designed to convert Ala363 into a termination codon in the wild-type esterase derived from Chromobacterium SC-YM-1.

What is claimed is:

1. A method of resolving 2-oxobicyclo[3.1.0]hexane-6-carboxylates having the following relative configuration of formula (1):

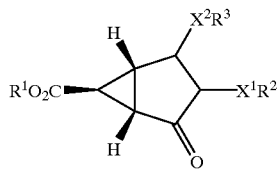

wherein $X^1$, $X^2$, $R^1$, $R^2$ and $R^3$ have the same meanings as defined below, into one enantiomer ester thereof and the other enantiomer acid, which comprises:
contacting an enzyme having an ability to preferentially hydrolyze one enantiomer ester contained in 2-oxobicyclo[3.1.0]hexane-6-carboxylate of formula (1) as defined above, with 2-oxobicyclo[3.1.0] hexane-6-carboxylate of formula (1) as defined above to obtain one enantiomer as an acid and the other enantiomer as an ester, wherein $R^1$ represents
a $C_1$ to $C_{10}$ alkyl group which may be substituted with at least one group selected from a $C_1$ to $C_8$ alkoxy, halogen or nitro;
an allyl group;
an arylalkyl group which aryl may be substituted with at least one group selected from a $C_1$ to $C_8$ alkyl, $C_1$ to $C_8$ alkoxy, halogen or nitro group; or
an aryl group which may be substituted with at least one group selected from a $C_1$ to $C_8$ alkyl, $C_1$ to $C_8$ alkoxy, halogen or nitro;

$X^1$ and $X^2$ independently represent a single bond, S, O, SO, $SO_2$ or $NR^4$ wherein $R^4$ represents a hydrogen or a group of formula: $(CO)nR^5$
wherein n is 0 or 1, and
$R^5$ represents hydrogen or a halogen atom;
a $C_1$ to $C_{10}$ alkyl group which may be substituted with at least one group selected from a C1 to C8 alkoxy, hydroxy, halogen, amino, nitro, thiol or thioalkyl;
a $C_2$ to $C_{10}$ alkenyl group which may be substituted with at least one group selected from a $C_1$ to $C_8$ alkoxy, hydroxy, halogen, amino, nitro, thiol or thioalkyl;
a $C_2$ to $C_{10}$ alkynyl group which may be substituted with at least one group selected from a $C_1$ to $C_8$ alkoxy, hydroxy, halogen, amino, nitro, thiol or thioalkyl;
an aryl group which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl;
an arylalkyl group which aryl may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl;
an aromatic heterocyclic ring which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl; or
a non-aromatic heterocyclic ring which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl;

$R^2$ and $R^3$ independently represent hydrogen, a halogen atom or a nitro group;
a $C_1$ to $C_{10}$ alkyl group which may be substituted with at least one group selected from a C1 to C8 alkoxy, hydroxy, halogen, amino, nitro, thiol or thioalkyl;
a $C_2$ to $C_{10}$ alkenyl group which may be substituted with at least one group selected from a $C_1$ to $C_8$ alkoxy, hydroxy, halogen, amino, nitro, thiol or thioalkyl;
a $C_2$ to $C_{10}$ alkynyl group which may be substituted with at least one group selected from a $C_1$ to $C_8$ alkoxy, hydroxy, halogen, amino, nitro, thiol or thioalkyl;
an aryl group which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl;
an arylalkyl group which aryl may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl;
an aromatic heterocyclic ring which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl;

a non-aromatic heterocyclic ring which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl;

a non-aromatic hydrocarbon ring which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl, said non-aromatic hydrocarbon ring being condensed with 1 or 2 aromatic hydrocarbon rings or aromatic heterocyclic rings; or a non-aromatic heterocyclic ring which may be substituted with at least one group selected from a $C_1$ to $C_8$ alkyl, $C_2$ to $C_8$ alkenyl, $C_2$ to $C_8$ alkynyl, $C_1$ to $C_8$ alkoxy, hydroxy, halogen, amino, nitro, thiol or thioalkyl, said non-aromatic heterocyclic ring being condensed with 1 or 2 aromatic hydrocarbon rings or aromatic heterocyclic rings.

2. The method according to claim 1, wherein 2-oxobicyclo[3.1.0]hexane-6-carboxylates having a relative configuration of formula (1'):

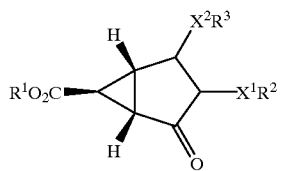

wherein $X^1$, $X^2$, $R^1$, $R^2$ and $R^3$ have the same meanings as defined in claim 1, is subjected to a reaction with the said enzyme to obtain one enantiomer acid resulting from one enantiomer ester contained in 2-oxobicyclo[3.1.0]hexane-6-carboxylate of formula (1) as defined in claim 1, and separating the other enantiomer ester of said resulting acid from the resulting mixture of diastereomeric esters.

3. The method according to claim 1 or 2, wherein $X^1$ and $X^2$ are single bonds, and $R^2$ and $R^3$ are hydrogen atoms in the 2-oxobicyclo[3.1.0]hexane-6-carboxylate of formula (1).

4. The method according to claim 1 or 2, wherein $R^1$ is a $C_1$ to $C_5$ alkyl group in the 2-oxobicyclo[3.1.0]hexane-6-carboxylate of formula (1).

5. The method according to claim 1 or 2, wherein said resulting enantiomer acid has an absolute configuration of formula (2b):

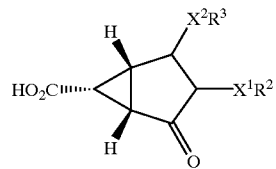

and said the other enantiomer ester has an absolute configuration of formula (3a);

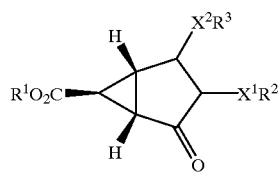

wherein $R^1$, $R^2$, $R^3$, $X^1$ and $X^2$ are the same as defined as defined in claim 1 or 2.

6. The method according to claim 1 or 2, wherein the enzyme is a hydrolase derived from microorganisms or a hydrolase derived from animals.

7. The method according to claim 6, wherein the enzyme is a hydrolase derived from microorganisms of the genus Achromobacter, Alcaligenes, Arthrobacter, Aspergillus, Bacillus, Burkholderia, Candida, Chromobacterium, Humicola, Mucor, Pseudomonas, or Rhizomucor.

8. The method according to claim 7, wherein the enzyme is a hydrolase derived from the microorganism Achromobacter sp., Alcaligenes sp., *Aspergillus melleus, Aspergillus oryzae*, Bacillus sp., *Bacillus licheniformis, Bacillus subtilis, Bacillus thermoglucosidasius, Burkholderia cepacia, Candida antarctica, Candida cylindracea, Candida rugosa, Chromobacterium viscosum*, Humicola sp., *Mucor miehei*, Pseudomonas sp., *Pseudomonas aeruginosa, Pseudomonas cepacia, Pseudomonas fluorescens*, or *Rhizomucor miehei*.

9. The method according to claim 8, wherein the enzyme is an esterase derived from FERMBP-6703 or FERMBP-3658.

10. The method according to claim 8, wherein the enzyme is a lipase derived from FERM BP-5740.

11. The method according to claim 1 or 2, wherein the enzyme is a hydrolase from the porcine kidney or bovine pancreas.

12. The method according to claim 7, wherein said enzyme is a mutant enzyme wherein one or a plurality of specific amino acids have been deleted, added or replaced.

13. The method according to claim 12 wherein said enzyme is a mutant enzyme having at least one mutation in the esterase gene contained in FERM BP-6703 selected from the following mutations, (a) 43rd Asn being replaced with Ser.

(b) 160th Gly being replaced with Ser.

(a) 189th Gly being replaced with Tyr, (d) 189th Gly being replaced with Phe, and (e) 363rd Ala being replaced with a terminal colon.

* * * * *

SEQUENCE LISTING

```
<160> NUMBER OF SEQ ID NOS: 11

<210> SEQ ID NO 1
<211> LENGTH: 30
<212> TYPE: DNA
<213> ORGANISM: Artificial sequence
<220> FEATURE:
<223> OTHER INFORMATION: Designed oligonucleotide primer to introduce
      the site-directed mutagenesis Asn43Ser  into the wild-type
      esterase from Chromobacterium SC-YM-1.

<400> SEQUENCE: 1
cagcgcggag gacacagacc cgtggacgaa                                      30

<210> SEQ ID NO 2
<211> LENGTH: 32
<212> TYPE: DNA
<213> ORGANISM: Artificial sequence
<220> FEATURE:
<223> OTHER INFORMATION: Designed oligonucleotide primer to introduce
      the site-directed mutagenesis Gly160Se r into the wild-type
      esterase from Chromobacterium SC-YM-1.

<400> SEQUENCE: 2
tgccggttgc ggtggcggca gtgcgaaccc cg                                   32

<210> SEQ ID NO 3
<211> LENGTH: 30
<212> TYPE: DNA
<213> ORGANISM: Artificial Sequence
<220> FEATURE:
<223> OTHER INFORMATION: Designed oligonucleotide primer to introduce
      the site-directed mutagenesis Gly189Ty r into the wild-type
      esterase from Chromobacterium SC-YM-1.

<400> SEQUENCE: 3
cgtcttccgc gccgtcatcg tcgcctcgga                                      30

<210> SEQ ID NO 4
<211> LENGTH: 30
<212> TYPE: DNA
<213> ORGANISM: Artificial sequence
<220> FEATURE:
<223> OTHER INFORMATION: Designed oligonucleotide primer to introduce
      the site-directed mutagenesis Gly189Ph e into the wild-type
      esterase from Chromobacterium SC-YM-1.

<400> SEQUENCE: 4
cgtcttccgc gccttcatcg tcgcctcgga                                      30
```

<210> SEQ ID NO 5
<211> LENGTH: 30
<212> TYPE: DNA
<213> ORGANISM: Artificial sequence
<220> FEATURE:
<223> OTHER INFORMATION: Designed oligonucleotide primer to change the
      Ala363 of the wild-type esterase from Chromobacterium SC-YM-1 to
      termination codon.

<400> SEQUENCE: 5
ccgccgaccg agtgaatcta aatccgctcc                                    30

<210> SEQ ID NO 6
<211> LENGTH: 28
<212> TYPE: DNA
<213> ORGANISM: Artificial sequence
<220> FEATURE:
<223> OTHER INFORMATION: Designed oligonucleotide primer to introduce
      the site-directed mutagenesis Asn43Ser  into the wild-type
      esterase from Chromobacterium SC-YM-1.

<400> SEQUENCE: 6
gaccatgatt acgaattctt ttttaata                                      28

<210> SEQ ID NO 7
<211> LENGTH: 30
<212> TYPE: DNA
<213> ORGANISM: Artificial sequence
<220> FEATURE:
<223> OTHER INFORMATION: Designed oligonucleotide primer to introduce
      the site-directed mutagenesis Gly160Se r, Gly189Tyr or Gly189Phe
      into the wild-type esterase from Chromobacterium SC-YM-1.

<400> SEQUENCE: 7
gaccacccgg tgctgagcct gaccctgcag                                    30

<210> SEQ ID NO 8
<211> LENGTH: 30
<212> TYPE: DNA
<213> ORGANISM: Artificial sequence
<220> FEATURE:
<223> OTHER INFORMATION: Designed oligonucleotide primer to change the
      Ala363 of the wild-type esterase from Chromobacterium SC-YM-1 to
      termination codon.

<400> SEQUENCE: 8
ggcggaacgg tcaccgaggt cgccgtcgag                                    30

<210> SEQ ID NO 9
<211> LENGTH: 30
<212> TYPE: DNA
<213> ORGANISM: Artificial sequence
<220> FEATURE:
<223> OTHER INFORMATION: Designed oligonucleotide primer to introduce
      the site-directed mutagenesis Asn43Ser  into the wild-type
      esterase from Chromobacterium SC-YM-1.

<400> SEQUENCE: 9
gtcgatgagg cgctggatga agtcggggtt                                    30

<210> SEQ ID NO 10
<211> LENGTH: 30
<212> TYPE: DNA
<213> ORGANISM: Artificial sequence
<220> FEATURE:
<223> OTHER INFORMATION: Designed oligonucleotide primer to introduce
      the site-directed mutagenesis Gly160Se r, Gly189Tyr or Gly189Phe

```
                          -continued into the wild-type esterase from Chromobacterium SC-YM-1.

<400> SEQUENCE: 10
tactgcgggg ccatggtgtt cagcacgccg                                   30

<210> SEQ ID NO 11
<211> LENGTH: 29
<212> TYPE: DNA
<213> ORGANISM: Artificial sequence
<220> FEATURE:
<223> OTHER INFORMATION: Designed oligonucleotide primer to change the
      Ala363 of the wild-type esterase from Chromobacterium SC-YM-1 to
      termination codon.

<400> SEQUENCE: 11
cgacggccag tgccaagctt gcatgccgc                                    29
```